(12) United States Patent
Bamford et al.

(10) Patent No.: US 12,336,100 B2
(45) Date of Patent: Jun. 17, 2025

(54) FLEXIBLE PRINTED CIRCUIT SENSOR

(71) Applicant: FONDAZIONE ISTITUTO ITALIANO DI TECNOLOGIA, Genoa (IT)

(72) Inventors: Simeon Asher Bamford, Castenuovo Berardenga (IT); Ella Janotte, Genoa (IT); Chiara Bartolozzi, Genoa (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 0 days.

(21) Appl. No.: 18/730,220

(22) PCT Filed: Jan. 17, 2023

(86) PCT No.: PCT/IB2023/050392
§ 371 (c)(1),
(2) Date: Jul. 18, 2024

(87) PCT Pub. No.: WO2023/139478
PCT Pub. Date: Jul. 27, 2023

(65) Prior Publication Data
US 2025/0142727 A1    May 1, 2025

(30) Foreign Application Priority Data

Jan. 19, 2022 (IT) ........................ 102022000000779

(51) Int. Cl.
*H05K 1/16* (2006.01)
*H05K 1/02* (2006.01)

(52) U.S. Cl.
CPC ............ *H05K 1/16* (2013.01); *H05K 1/0277* (2013.01); *H05K 2201/10151* (2013.01)

(58) Field of Classification Search
CPC .................. H05K 1/16; H05K 1/0277; H05K 2201/10151
See application file for complete search history.

(56) References Cited

U.S. PATENT DOCUMENTS

2007/0273394 A1   11/2007   Tanner et al.
2011/0283821 A1   11/2011   Ober et al.
(Continued)

OTHER PUBLICATIONS

International Search Report and Written Opinion, mailed May 3, 2023, from PCT International Application No. PCT/IB2023/050392, 12 pages.
(Continued)

*Primary Examiner* — Hoa C Nguyen
(74) *Attorney, Agent, or Firm* — Workman Nydegger

(57) ABSTRACT

A flexible printed circuit flex-PCB sensor includes a sheet of electronically printable flexible material, sensor cells printed on said sheet and each including a sensitive element and a circuit. Each sensitive element is arranged to measure a predetermined physical parameter and to obtain an associated measurement signal. Each circuit is arranged to receive and process the measurements signal in order to obtain a corresponding output signal. Communication means are arranged to transmit the digital signals coming from said sensor cells to a remote processing circuit. The sheet is coiled according to a three-dimensional shape having a layered structure. Layers of said sheet are placed side by side and form a sensing border that is substantially perpendicular to the surface of said sheet. The relative position of each sensitive element and of each circuit inside the sensor relative to said sensing border depends on their relative position thereof.

10 Claims, 16 Drawing Sheets

(56) References Cited

U.S. PATENT DOCUMENTS

| | | | | |
|---|---|---|---|---|
| 2018/0180684 A1* | 6/2018 | Govari | ............... | H05K 1/115 |
| 2019/0051639 A1* | 2/2019 | Hussain | ............... | H05K 1/0386 |
| 2019/0117083 A1* | 4/2019 | Wang | ............... | A61B 5/6833 |
| 2021/0076975 A1* | 3/2021 | Gliner | ............... | H05K 1/165 |
| 2021/0177355 A1* | 6/2021 | Govari | ............... | A61B 5/0538 |
| 2021/0353184 A1 | 11/2021 | Guery et al. | | |
| 2022/0037054 A1* | 2/2022 | Karicherla | ............... | H05K 3/4682 |
| 2023/0031505 A1* | 2/2023 | Yamagishi | ............... | A61B 5/6833 |
| 2023/0248610 A1* | 8/2023 | Kim | ............... | A61H 23/0245 |
| | | | | 601/2 |

OTHER PUBLICATIONS

Oh H. et al., "Scalable tactile sensor arrays on flexible substrates with high spatiotemporal resolution enabling slip and grip for closed-loop robotics", Science Advances, vol. 6, Issue 46, eabd7795, Nov. 13, 2020, 14 pages.

Finateu et al., "5.10 A 1280×720 Back-Illuminated Stacked Temporal Contrast Event-Based Vision Sensor with 4.86μm Pixels, 1.066GEPS Readout, Programmable Event-Rate Controller and Compressive Data-Formatting Pipeline", IEEE International Solid-State Circuits Conference, Feb. 1, 2020.

Colonnier et al., "A small-scale hyperacute compound eye featuring active eye tremor: application to visual stabilization, target tracking, and short-range odometry", Bioinspiration & Biomimetics, vol. 10, Feb. 25, 2015, : 026002.

Marcus, "A new coiled microspring contact technology," 2001 Electronic Components and Technology Conference (Cat. No. 01CH37220), 2001, pp. 1227-1232, doi: 10.1109/ECTC.2001.927985.

Münzenrieder N. et al., "Stretchable and conformable oxide thin-film electronics", Advanced Electronic Materials, vol. 1, Mar. 2015, 1400038, 7 pages.

Bragg L. et al., "Field Sampling with a Polydimethylsiloxane Thin-Film", Journal of Chromatographic Science, vol. 44, Jul. 2006, pp. 317-323.

Lee G. et al., "Nature-inspired rollable electronics", NPG Asia Materials, vol. 11, Issue 67, Nov. 22, 2019, 10 pages.

Yamaoka J. et al., "FoldTronics: Creating 3D objects with integrated electronics using foldable honeycomb structures", 2019 CHI Conference on Human Factors in Computing Systems Proceedings, May 4-9, 2019, pp. 1-14.

Sheng J. et al., "Review of recent advances in flexible oxide semiconductor thin-film transistors", Journal of Information Display, 18:4, Oct. 19, 2017, pp. 159-172, DOI: 10.1080/15980316.2017.1385544.

Büchel J. et al., "Network insensitivity to parameter noise via adversarial regularization", Jun. 9, 2021 arXiv:2106.05009.

Kwon J. et al., "Three-dimensional monolithic integration in flexible printed organic transistors", Nature Communications, Jan. 3, 2019, 10:54, 10 pages.

\* cited by examiner

Fig.16
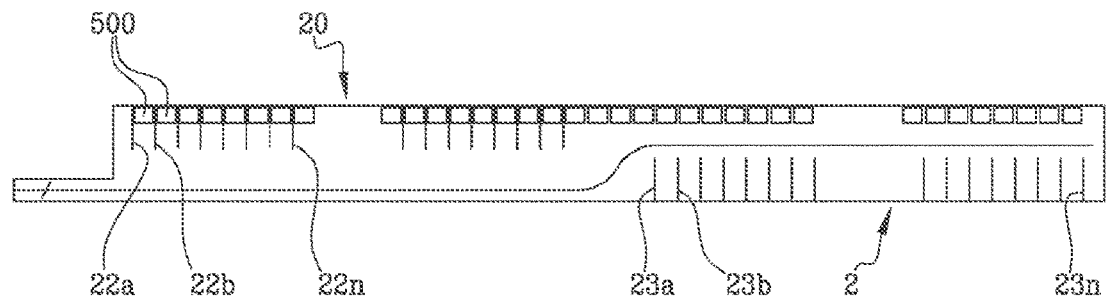
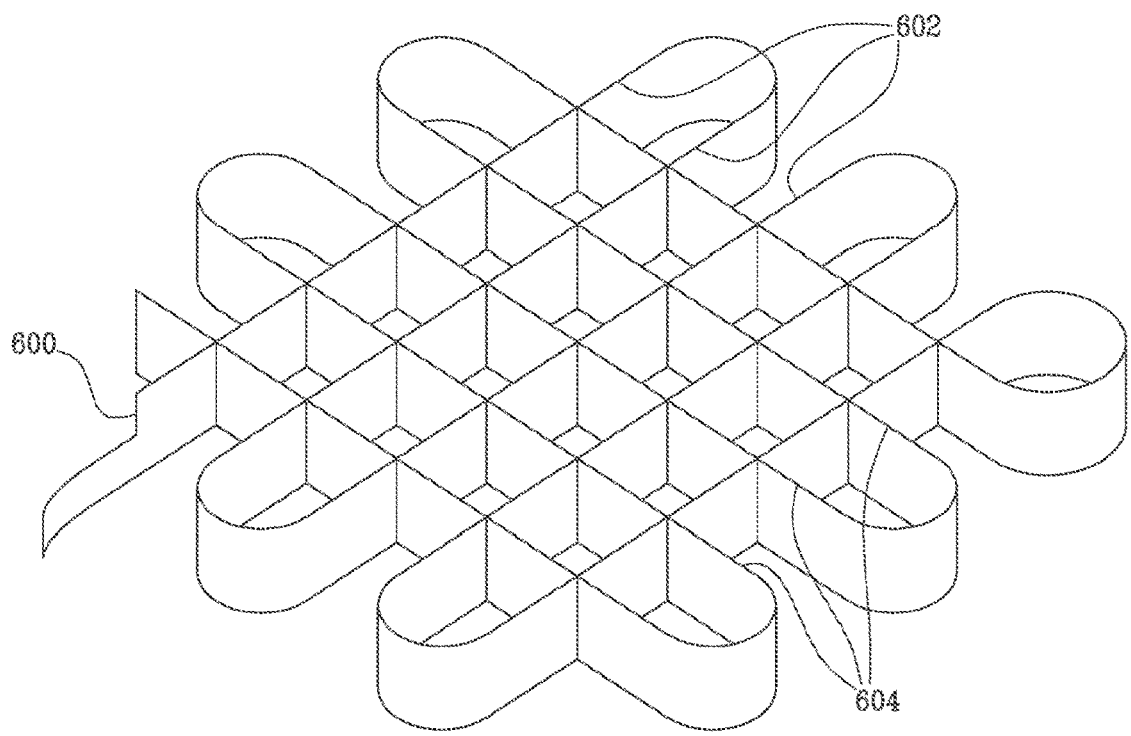
Fig.17

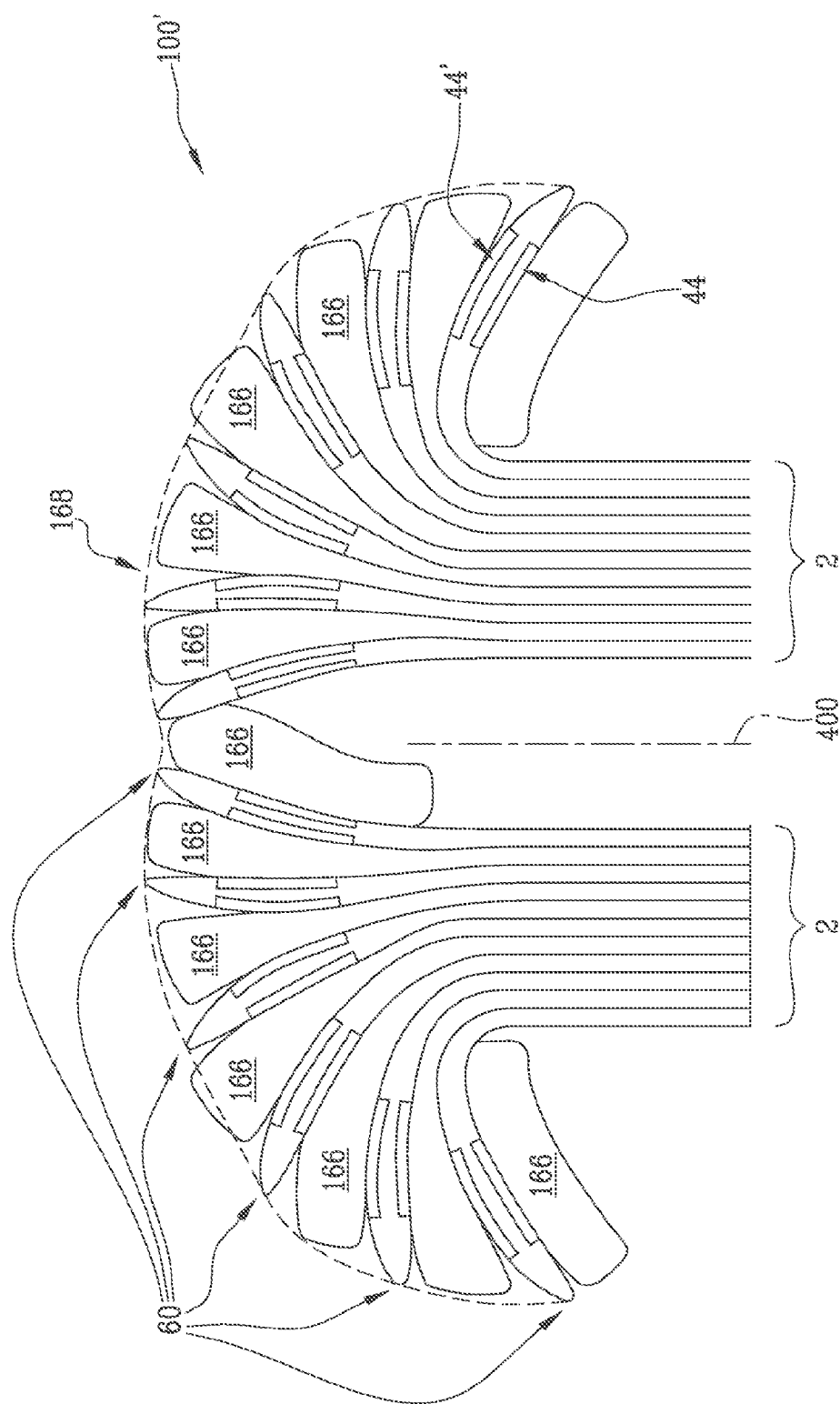

FLEXIBLE PRINTED CIRCUIT SENSOR

BACKGROUND

Background and Relevant Art

The present invention relates to a flexible printed circuit sensor, in particular a sensor with a three-dimensional configuration based on a two-dimensional flexible printed circuit sensor.

There are known modern microtechnological sensors that include multiple sensitive elements, for example the "taxels" of tactile sensors or the "pixels" of image sensors. According to the predominant design for electronics, circuits that transduce, process and communicate signals coming from sensors are typically arranged in one-dimensional or two-dimensional arrays placed on the surface of a microchip. Transistors (MOSFETs) or other basic electronic components such as diodes are typically produced on the surface of a microchip with a photolithography process, and serve as elements of transduction, processing, and communication circuits of a sensor.

Sometimes these components also function as sensing elements themselves, as in the case of "POSFETs" (piezo-active MOSFETs), "ChemFETs" (chemically sensitive MOSFETs) and photodiodes (Oh H., Yi G. C., Yip M. and Dayeh S. A., 2020, "Scalable tactile sensor arrays on flexible substrates with high spatiotemporal resolution enabling slip and grip for closed-loop robotics", Science Advances, 6(46), p.eabd7795).

Such microelectromechanical (MEM) sensing elements can also be integrated onto the surface of a microchip.

The placement of sensitive elements (sensing elements) together with signal transduction and processing elements has advantages compared to the alternative of producing sensitive elements separate from the transduction and processing circuits, such as, for example: reduction of the complexity of wiring through multiplexing, parallel signal processing to reduce system latency, better signal fidelity, data filtering and compression and savings in sensor production costs.

When the surface of the microchip on which the sensitive elements and transduction, processing and communication circuits are placed is also used as a sensitive surface, it is exposed to environmental influences. This exposure can create problems, including the unintended influence of the environment on the circuits' behaviour, for example the effects of light, heat and pressure on the transistors. Such exposure can also potentially damage the circuits or the wiring thereof.

A further drawback is the need for the surface to be shared among the sensors and the respective circuits: this leads to a less compact design and sometimes also to a reduction in the intensity of the detected signal.

One possibility for overcoming these limitations consists in creating three-dimensional "stacked" integrated circuits. With this approach, multiple layers of active electronic devices are produced and connected to one another by means of metallic interconnections between the layers. Present in these systems there is a through-layer of silicon and a plurality of arrays, which allow parallel processing in each of a series of processing circuits distributed over one or more vertically stacked layers (Finateu, Niwa, Matolin, Tsuchimoto, Mascheroni, Reynaud, Mostafalu, Brady, Chotard, LeGoff, Takahashi, Wakabayashi, Oike, Posch 5.10 A 1280×720, "Back-Illuminated Stacked Temporal Contrast Event-Based Vision Sensor with 4.86 µm Pixels", 1.066GEPS Readout, Programmable Event-Rate Controller and Compressive Data-Formatting Pipeline, 2020 IEEE International Solid-State Circuits Conference—(ISSCC)).

The sensing elements thus occupy an outer layer of the resulting multilayer, whereas other circuits are removed from the sensor surface.

One-dimensional or two-dimensional sensor arrays are also produced on printed circuit boards (PCBs).

This approach shares all the advantages and problems listed above for integrated microcircuit solutions; however, the sensing elements and the respective circuits can be prefabricated devices of arbitrary complexity, which are later bonded to the printed circuit boards at the cost of using a larger area.

Traditional printed circuit boards are rigid; however, they can also be flexible and extendable (hereinafter "flex-PCBs"). This flexibility is proving to be useful in many fields of application, including tactile sensing. Flex-PCB-type devices are today also being applied in other sectors, including visual sensing (Colonnier, F. et al., "A small-scale hyperacute compound eye featuring active eye tremor: application to visual stabilization, target tracking, and short-range odometry", *Bioinspiration & Biomimetics* 10.2 (2015): 026002).

Coiled or spiral wound flex-PCB sensors for producing three-dimensional sensing elements are known (R. B. Marcus, "A new coiled microspring contact technology," 2001 Proceedings, 51st Electronic Components and Technology Conference (Cat. No. 01CH37220), 2001, pp. 1227-1232, doi: 10.1109/ECTC.2001.927985), as are flex-PCB sensors shaped in a third dimension by following an accordion-like design to improve the elasticity thereof when attached to skin (Munzenrieder N., Cantarella G., Vogt C., Petti L., Büthe L., Salvatore G. A. and Tröster G. (2015), "Stretchable and conformable oxide thin-film electronics. Advanced Electronic Materials", 1(3), 1400038) or coiled flex-PCB sensors to cover the inside of tubes for chemical detection (Bragg L., Qin Z., Alaee M., Pawliszyn J., "Field Sampling with a Polydimethylsiloxane Thin-Film", (2006), *Journal of Chromatographic Science*, Vol. 44, page 317).

The characteristics of flex-PCB sensors have been exploited for active sensing (Lee G., Choi Y. W., Lee T., Lim K. S., Shin J., Kim T., Kim H. K., Koo B. K., Kim H. B., Lee J. G., Ahn K., "Nature-inspired rollable electronics", *NPG Asia Materials*. 2019 Nov. 22; 11(1):1-0) or to construct three-dimensional electronic systems using construction models derived from traditional paper folding arts (Yamaoka J., Dogan M. D., Bulovic K., Saito K., Kawahara Y., Kakehi Y., Mueller S., FolDTronics Demo, "Creating 3D objects with integrated electronics using foldable honeycomb structures", in Extended Abstracts of the 2019 CHI Conference on Human Factors in Computing Systems 2019 May 2 (pp. 1-4)).

However, only a small part of this potentially large design space has been explored to date.

Thin-film transistors (TFTs) can also be produced on a flexible PCB with photolithography techniques, inkjet printing, rotogravure printing, etc. (Sheng J., Jeong H. J., Han K. L., Hong T., Park J. S., 2017, "Review of recent advances in flexible oxide semiconductor thin-film transistors", *Journal of Information Display*, 18:4, 159-172, DOI: 10.1080/15980316.2017.1385544).

Comparing the most advanced technologies, TFTs are considered to be inferior to MOSFETs produced on molten silicon based on various factors, including larger dimensions, reduced speed and gain, less reliability and higher variability among devices.

However, production through a printing process allows potential advantages, including ease of access to the technology and the speed of iteration of the process.

Recently, a series of methods have also been developed in the field of neural and neuromorphic computing, whereby the computation can be rendered insensitive to device variation (Büchel J., Faber F., Muir D. R., "Network insensitivity to parameter noise via adversarial regularization", 2021 arXiv: 2106.05009).

At times the sensors benefit from the positioning of the sensitive elements at different depths and with different orientations within the sensor itself: in biology, for example, one finds mechanoreceptors placed at different depths within the skin and activated by lateral forces, sometimes accentuated by the presence of hairs or skin of varying elasticity; in electronics it is known that the frequency response curve of a silicon photodiode with respect to incident light varies according to the depth through which the light must first penetrate.

In addition to chip stacking technology, additive manufacturing is a promising field for the construction of three-dimensional structures that include wiring, i.e. structures like antennas printed in three dimensions. It is also possible to construct active devices such as transistors using this technology (Kwon J., Takeda Y., Shiwaku R., Tokito S., Cho K., Jung S., "Three-dimensional monolithic integration in flexible printed organic transistors", *Nature Communications*. 2019 Jan. 3; 10(1):1-0).

Among the many opportunities offered by flexible printed electronics and organic TFTs, there is the possibility of creating completely biodegradable sensors and other electronic devices that can be distributed in the natural environment in a safe and sustainable manner.

The main problems and disadvantages of the technologies presented above are:
- complexity of the wiring in the event that the sensor arrays are manufactured separately from the transduction, processing and communication circuits;
- lack of physical flexibility devices of molten silicon devices and traditional PCBs, which limits the morphological adaptation to different problematic domains;
- exposure of circuits present on the substrate of two-dimensional sensors to environmental influences;
- competition for space on the surface of the two-dimensional sensor, to be divided between sensitive elements and the respective circuits and wiring;
- complexity and immaturity of three-dimensional printing technology; and
- environmental impact of sensors when discarded in the natural environment.

BRIEF SUMMARY

The object of the present invention is thus to propose an innovative flexible printed circuit sensor that overcomes the problems of the prior art.

This and other objects are achieved with a flexible printed circuit sensor whose main features are defined in claim 1.

Particular embodiments form the subject matter of the dependent claims, whose content is to be considered as an integral part of this this description.

DESCRIPTION OF THE DRAWINGS

Additional features and advantages of the invention will become apparent from the detailed description that follows, provided purely by way of non-limiting example, with reference to the appended drawings, in which:

FIG. 16 shows a flex-PCB sensor similar to the one in FIG. 1;

FIG. 17 shows a three-dimensional structure that uses the flex-PCB sensor in FIG. 16;

FIG. 21 shows a cross sectional view of the flex-PCB sensor in FIG. 20.

DETAILED DESCRIPTION

Figure 1:
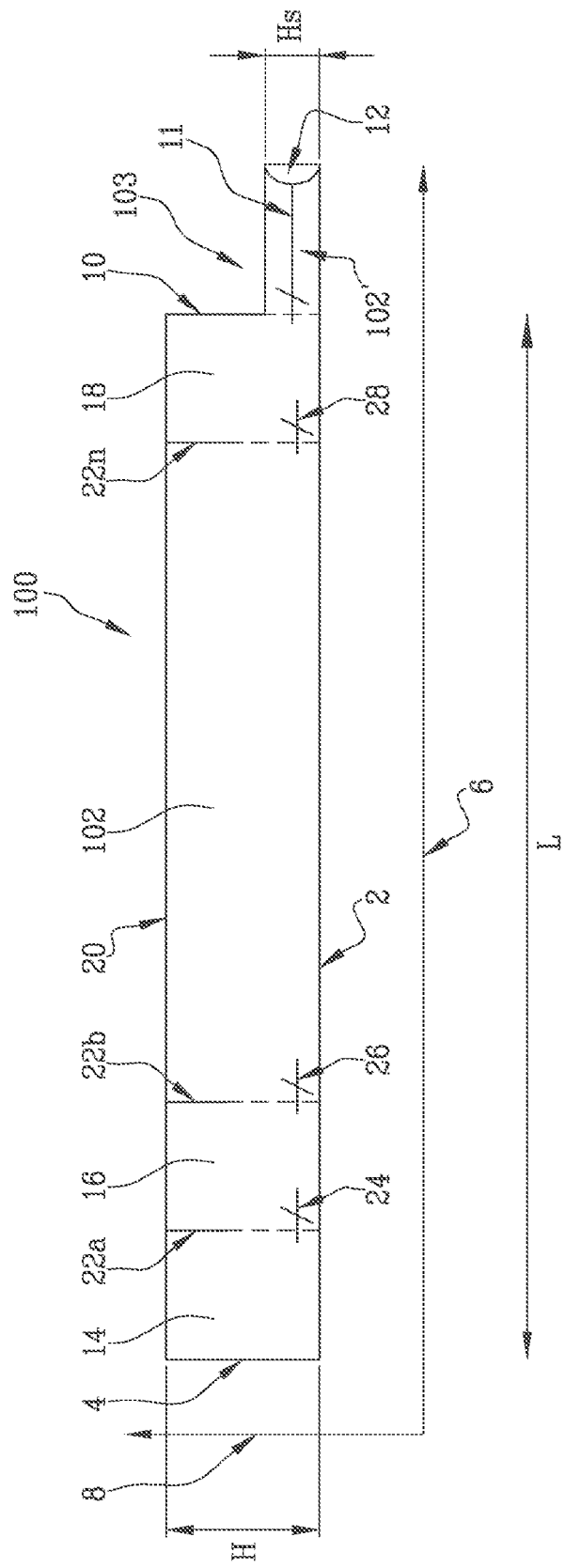
FIG. 1 shows a top view of a flexible printed circuit flex-PCB sensor according to the present invention.

In summary, the flexible printed circuit sensor according to the present invention is a sensor printed on a flexible two-dimensional (flex-PCB) substrate wherein a plurality of sensing elements (sensitive elements) are placed together with circuits necessary for the transduction, processing and communication of signals coming from the sensitive elements following measurements of predetermined physical parameters.

The sensitive elements are arranged to measure a predetermined physical parameter, for example a pressure exerted on the sensor, and to obtain an associated measurement signal therefrom.

The circuits contain active devices, preferably printed with thin-film transistor technology.

The sensing elements placed together with the respective circuits on the flexible substrate will hereinafter be indicated as "sensor cell".

The sensor cells are connected to one another thanks to communication elements. The sensor cells are preferably arranged in matrices of one or two dimensions; however, different positionings are also possible.

One or more sensor cells are arranged on a single flexible flex-PCB substrate, and one or more layers of flexible flex-PCB substrates can be coiled (or otherwise inserted into a three-dimensional structure such as, for example, a spiral structure or an accordion-like structure) so as to have a local arrangement, relative to one another, that is prevalently laminar.

The coiled three-dimensional structure is produced in a configuration step following printing, but it is also possible to use two-dimensional flex-PCB substrates already layered following a preliminary printing process and subsequently coil them to create the three-dimensional structure.

A sensing border of such a coiled structure thus consists of the individual sides or borders of several coiled layers placed side by side. The layers must not be touched and consequently this sensing border need not be solid. Different two-dimensional shapes of flexible flex-PCB substrates can be used to create arbitrarily complex three-dimensional surfaces, including fractal surfaces.

Environmental influences such as pressure, light, heat, chemical concentrations etc. pass across this border to influence the sensitive elements. The sensitive elements can be positioned at different depths relative to the border to have possible advantages in sensing.

When the circuits associated with the sensitive elements are placed at greater depths than the sensitive elements, they can benefit from a protection against environmental influences, the sensitive elements can also benefit from a controllable balance between sensitivity and protection.

A first embodiment of a flexible printed circuit sensor according to the present invention will now be described, a tactile sensor which uses a combination of different types of sensitive elements, such as piezoelectric sensors and capacitive distance measuring sensors, to provide real-time multichannel information about the pressure exerted on the three-dimensional border of the sensor.

FIG. 1 shows a top view of a flexible printed circuit flex-PCB sensor 100 according to the present invention.

The flex-PCB sensor 100 comprises a sheet of electronically printable flexible material 102, for example PEN (polyethylene naphthalate), preferably with a thickness of less than 50 µm. Alternatively, the sheet is made of SEBS (styrene-ethylene-butadiene-styrene).

The two-dimensional shape of the sheet 102 is prevalently rectangular, having a first side 2 (first dimension) and a second side 4 (second dimension).

A first and a second axis 6 and 8 of a Cartesian reference system are included in FIG. 1 to highlight that the first side 2 is aligned with the first axis 6 (x axis) whereas the second side 4 is aligned with the second axis 8 (y axis) perpendicular to the first axis 6.

The second side 4 will also be indicated as the inner side to distinguish it from a third side or opposite outer side 10.

In a lateral area 103 of the flex-PCB sensor 100 there is a protuberance 102' of the sheet 102 which extends along the first axis 6 relative to a width L of the flex-PCB sensor 100 and has a height $H_s$ along the second axis 8 which is less than a height H of the flex-PCB sensor 100.

The protuberance 102' accommodates a connection bus 11 directed towards a remote processing circuit by means of a connector 12.

The flex-PCB sensor 100 comprises a first sensor cell 14, a second sensor cell 16 and so on up to a last sensor cell 18.

The reference 20 indicates a fourth side of the flex-PCB sensor 100 opposite the first side 2, which will also be called the sensitive side because it is used to form the sensitive border of the flex-PCB sensor 100, as detailed below.

The first side 2 is also called the circuit side, because the transduction, processing and communication circuits are positioned towards this side of the flex-PCB sensor 100.

The boundaries between adjacent sensor cells 14, 16, . . . , 18 are shown with broken lines. Advantageously, the flex-PCB sensor 100 can further comprise a plurality of cuts 22a, 22b, . . . , 22n, perpendicular to the sensitive side 20 and located at the respective boundaries between adjacent sensor cells 14, 16, . . . 18, starting from the sensitive side 20 and extending towards the circuit side 2. The cuts 22a, 22b, . . . , 22n are shown with solid lines.

The flex-PCB sensor 100 further comprises a first communication bus 24 that joins the first sensor cell 14 and the second sensor cell 16, a second communication bus 26 that joins the second sensor cell 16 to an adjacent sensor cell, etc. The sensor measurements can thus pass from the first sensor cell 14 to the second sensor cell 16 through the first communication bus 24, from the second sensor cell 16 to the adjacent sensor cell through the second communication bus 26 and so on, until arriving at the connector 12 through the connection bus 11.

Alternatively, the wires of the first communication bus 24, the second communication bus 26, etc. up to a last communication bus 28 are continuous and used for a communication shared by means of a multiplexing protocol or to carry a power supply from the connector 12 to the first sensor cell 14, the second sensor cell 16, etc., up to the last sensor cell 18.

Figure 2:
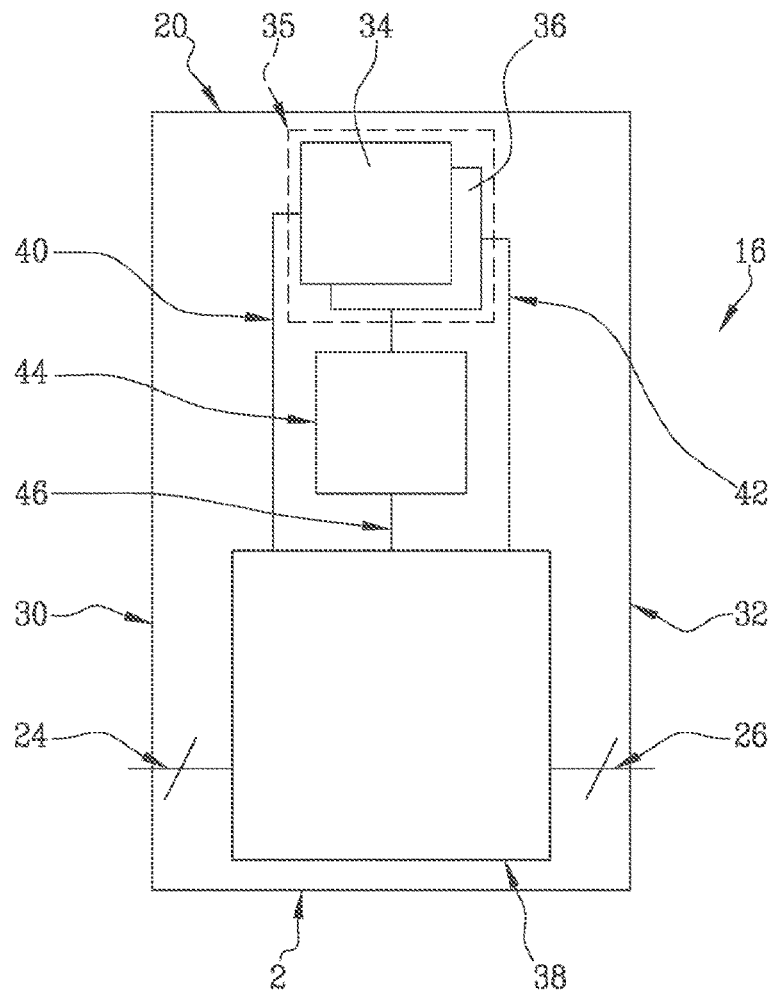
FIG. 2 shows a top view of a sensor cell.

FIG. 2 shows a top view of a sensor cell, for example the second sensor cell 16, in which the references 30 and 32 indicate two sides forming a boundary with respective adjacent sensor cells, 34 and 36 indicate a first and a second plate of conductive material, preferably metal, applied on top of one another using a printing process, in itself known, that enables the production of two or more metal layers. Present between the first plate 34 and the second plate 36 there is a thin layer of piezoelectric material, for example P(VDF-TrFE). The first plate 34 and the second plate 36 together form a sensing element or sensitive element 35, in particular a piezo-capacitor, in itself known.

The second sensor cell 16 further comprises a circuit 38 that transduces and processes measurement signals coming from the sensitive element 35 into output signals, preferably digital signals, suitable for being transmitted along the second communication bus 26 towards a corresponding circuit placed in an adjacent sensor cell downstream (towards the right) of the flex-PCB sensor 100, whereas the first communication bus 24 is suitable for carrying the digital signals in the opposite direction towards the first sensor cell 14.

The digital signals processed by the circuit 38 are suitable for being sent, by means of adjacent sensor cells 14, 16, . . . , 18, to the remote processing circuit through said connector 12.

If the first communication bus 24 is a communication channel that is separate from the second communication bus 26, the circuit 38 also performs the role of a controller between the digital signals arriving along the first communication bus 24 and the digital signals generated by the second sensor cell 16. Two wires 40 and 42 respectively connect the first plate 34 and the second plate 36 to the circuit 38.

Therefore, each sensor cell 14, 16, . . . , 18 comprises a sensitive element 35 arranged to measure a predetermined physical parameter and to obtain an associated measurement signal, and each circuit 38 is arranged to receive said measurement signal and to process it in order to obtain a corresponding output signal to be transmitted to the remote processing circuit.

The second sensor cell 16 further comprises an additional metal plate 44, which represents an additional sensitive element, placed farther away from the sensitive side 20 than the sensitive element 35 but closer thereto than the circuit 38 and connected to the circuit 38 by means of a connecting wire 46.

Figure 3:
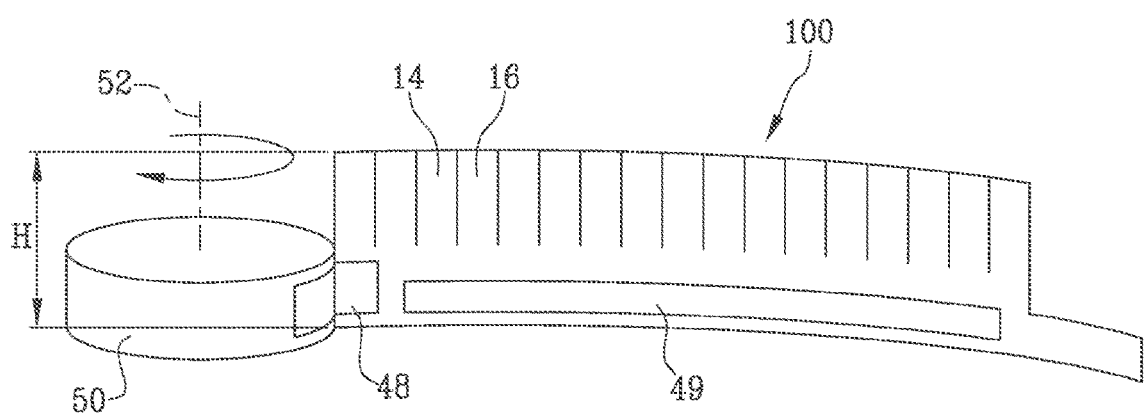
FIG. 3 shows a top view of the flex-PCB sensor in FIG. 1 connected to a cylindrical winding body.

FIG. 3 shows a top view of the flex-PCB sensor 100 in FIG. 1, on which a first adhesive tape 48 has been attached, at the second side 4, to connect the flex-PCB sensor 100 to a cylindrical winding body 50 (hereinafter called cylindrical jig). The height of the cylindrical jig 50 is less than the height H of the flex-PCB sensor 100. Once fixed, the cylindrical jig 50 is suitable for rotating about its own rotation axis 52 so as to wind the flex-PCB sensor 100 around it.

A second adhesive tape 49 is applied on the surface of the flex-PCB sensor 100 so that, once the flex-PCB sensor 100 is wound on the cylindrical jig 50, different parts of the flex-PCB sensor 100 wound into a coil attach to one another, thereby forming superimposed layers. The second adhesive tape 49 is positioned under the circuit 38 or is placed on top of the circuit 38 so as to make the structure more robust in proximity to said circuit 38.

Figure 4:
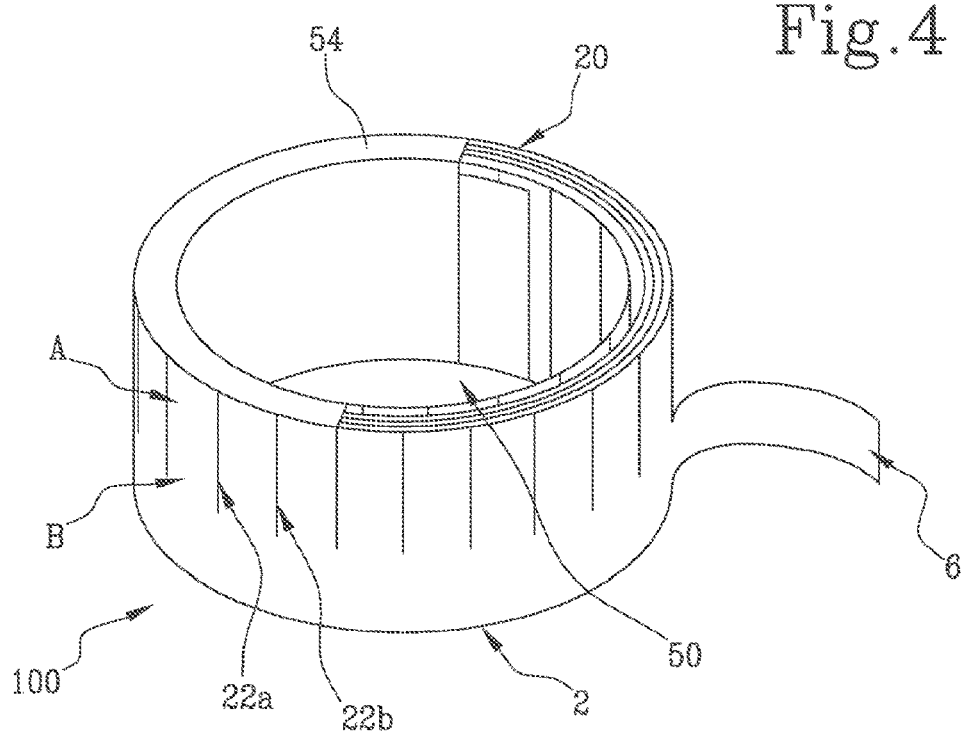
FIG. 4 shows a perspective view of the flex-PCB sensor in FIG. 1 wound into a coil.

FIG. 4 shows a perspective view of the flex-PCB sensor 100 in FIG. 1 wound into a coil.

The sensitive side 20 now forms a sensing border 54 of the flex-PCB sensor 100. The sensing border 54 is not a solid, complete surface, but corresponds to the zone defined by the placement of the sensitive sides 20 of the flex-PCB sensor 100 side by side in the three-dimensional space. In FIG. 4 the sensing border 54 is shown only partially in order to highlight said sensitive sides 20 placed side by side in the other portion of the circle representing the coiled flex-PCB sensor 100. The cylindrical jig 50, located inside the winding of the flex-PCB sensor 100, must not reach that sensing border 54.

A zone A of the outer surface of the winding of the flex-PCB sensor 10, positioned near the sensing border 54, does not have the jig 50 positioned behind it inside the winding of the flex-PCB sensor 100. A zone B of the outer surface of the winding of the flex-PCB sensor 100, positioned towards the circuit side 2 of the flex-PCB sensor 100, has the cylindrical jig 50 positioned behind it.

Zone A is adapted to deform towards the inside more easily than zone B if subjected to pressure from outside the winding of the flex-PCB sensor 100 towards the inside. This is due in part to the fact that the internal support of the cylindrical jig 50 is missing and in part to the fact that the partial cuts 22a, 22b, . . . , 22n of the sheet 102 located at the sensor cells 14, 16, . . . , 18 lend the portions of the sheet 102 occupied by each sensor cell 14, 16, . . . , 18 a certain physical independence from one another, so that they do not support one another and bend more easily. Therefore, the portion of the flex-PCB sensor 100 occupied by the sensing elements of each sensor cell 14, 16, . . . 18 is more bendable than the part of the flex-PCB sensor 100 occupied by the respective circuits 38 and by the communication bus 24, 26, . . . 28. The diameter of the cylindrical jig 50 is selected so as to comply with a minimum radius of curvature necessary to ensure the integrity of the circuits 38 of the various sensor cells 14, 16, . . . , 18 and of the wiring along the winding of the coiled flex-PCB sensor 100.

Figure 5:
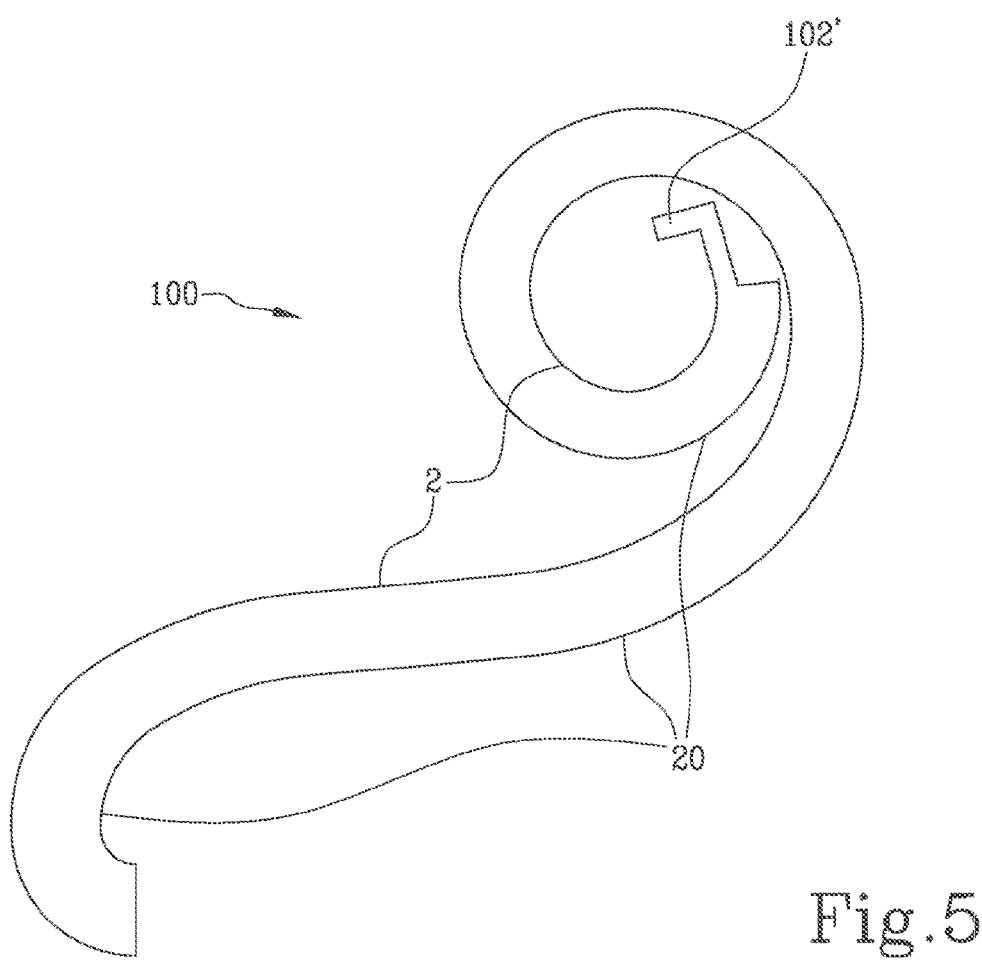
FIG. 5 shows a top view of an alternative embodiment of the flex-PCB sensor in FIG. 1.

FIG. 5 shows a top view of an alternative embodiment of the flex-PCB sensor 100 in FIG. 1.

Although it is topologically identical to the flex-PCB sensor 100 in FIG. 1, it has been bent into a spiral shape such that, when the flex-PCB sensor 100 is coiled, the sensitive side 20 forms a hemispherical cap as detailed below.

Figure 6:
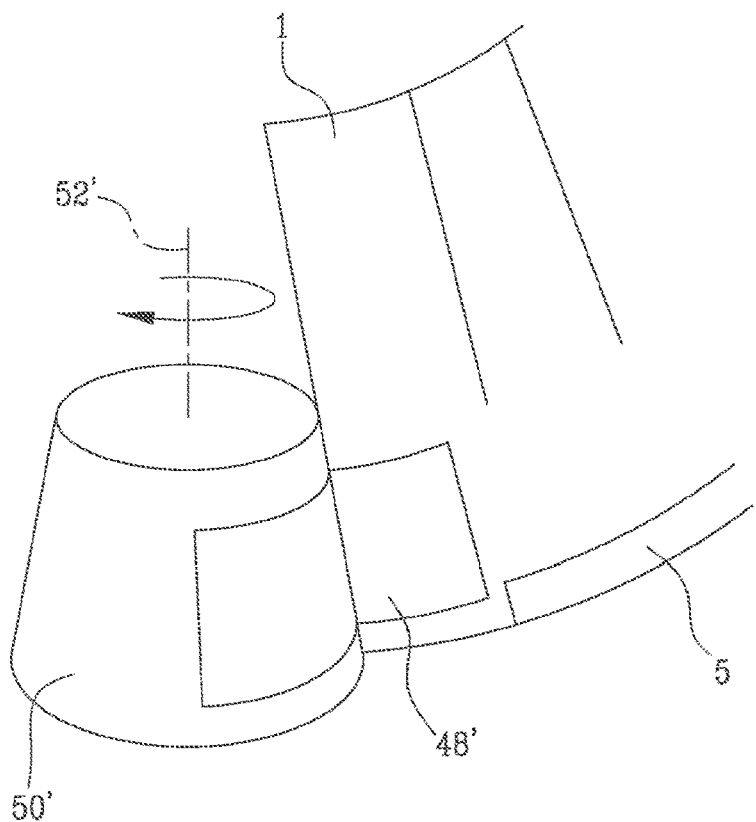
FIG. 6 shows an enlargement of the flex-PCB sensor in FIG. 5.

FIG. 6 shows an enlargement of the flex-PCB sensor 100 in FIG. 5 on which an adhesive tape 48' has been attached to connect it to a truncated cone-shaped jig 50'. The reference 52' indicates the rotation axis about which the truncated cone-shaped jig 50' rotates to wind the flex-PCB sensor 100. The adhesive 48' is positioned at the circuit side 2 of the flex-PCB sensor 100, so that the circuit side 2 is well packed with the solid support of truncated cone-shaped jig 50'.

Figure 7:
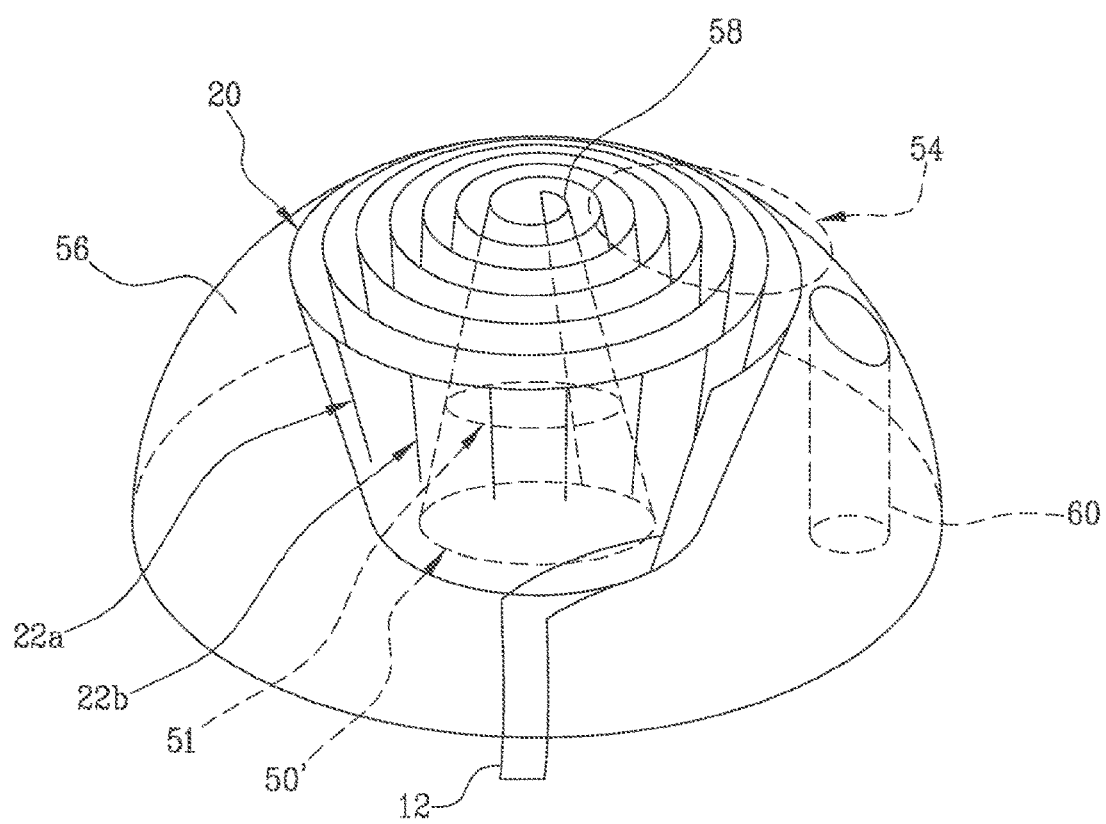
FIG. 7 shows a perspective view of the winding of the three-dimensional flex-PCB sensor.

FIG. 7 shows a perspective view of the winding of the three-dimensional flex-PCB sensor 100, whose sensitive side 20 forms a hemispherical cap 56. The flex-PCB sensor 100 is first wound and then inserted upside-down in a hemispherical mould, finally, a two-component silicone rubber, with an improved dielectric constant compared to the air it replaces, is introduced into the mould so that the flex-PCB sensor 100 is inserted inside a solid elastomeric hemisphere 56. The base of the truncated cone-shaped jig 50' is shown with a broken line and its upper face is shown with a broken line 51. The upper radius 58 of an upper projection of the truncated cone-shaped jig 50' is such as to comply with a minimum radius of curvature for the protection of wires, TFT, etc. If the upper radius 58 falls below a minimum threshold value, the cuts 22a, 22b, . . . , 22n will offer a certain degree of protection to the wiring.

A solid rod 60 is adapted to penetrate into the elastomeric hemisphere 56 and this is shown exclusively to indicate that the physical assembly and internal flexibility of the flex-PCB sensor 100 and its response to the external load can be influenced and controlled mechanically from the outside.

Figure 8:
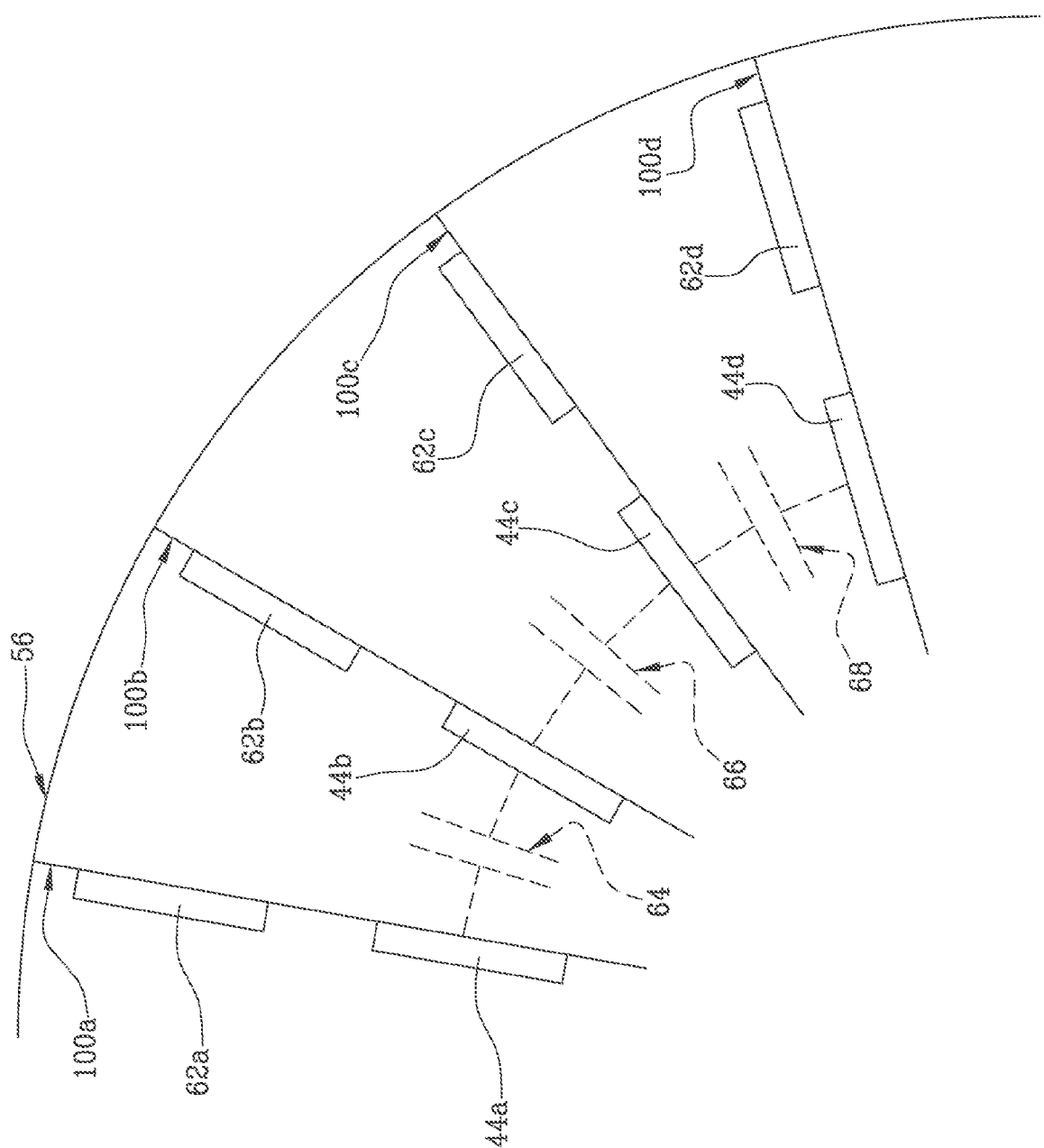
FIG. 8 shows a cross sectional top view of the hemispherical cap in FIG. 7.

FIG. 8 shows a lateral cross section of the hemispherical cap 56 in FIG. 7, in which one may see four layers 100a, 100b 100c and 100d of the flex-PCB sensor 100, four sensitive elements 62a, 62b, 62c and 62d (each corresponding to the sensitive element 35 in FIG. 2), constructed as described above with reference to FIG. 2, and four additional metal plates 44a, 44b, 44c and 44d, printed respectively on the surfaces of the layers 100a, 100b 100c and 100d of the flex-PCB sensor 100.

The sensing border 54 of the flex-PCB sensor 100 is represented by the surface of the hemispherical cap 56. The layers 100a, 100b 100c and 100d are shown as perpendicular to the surface 56 in order to represent this concept, however, the layers 100a, 100b 100c and 100d could intersect the surface of the hemispherical cap 56 with any angle of incidence.

A first sensitive element 62a and a first additional metal plate 44a are mounted on a first layer 100a, whilst a second additional metal plate 44b is mounted on a second layer 100b, which is adjacent to the first layer 100a. The additional metal plates 44a and 44b lie approximately parallel to each other and together form a first capacitor, whose circuit symbol is indicated with the reference 64. Similarly, other circuit symbols 66 and 68 relating to the capacitors formed by the other layers 100c and 100d are shown. The second additional metal plate 44b thus forms more than one capacitor, as does the third additional metal plate 44c and so on. The additional metal plates 44a-44d collectively form a capacitive network. Although FIG. 8 shows a prevalently one-dimensional capacitive network, by varying the positions and shapes of several metal plates in the two main dimensions of the flex-PCB sensor 100, it is possible to obtain arbitrarily complex capacitive networks of up to three dimensions. Since the first additional metal plate 44a and the second additional metal plate 44*b* are connected to distinct respective circuits (not shown in the figure), which are not positioned side by side on the surface of the sheet 102 of the flex-PCB sensor 100, the measurement of the capacitance of the first capacitor 64 requires cooperation among long-range circuits through the circuits 38 of the flex-PCB sensor 100.

Figure 9:
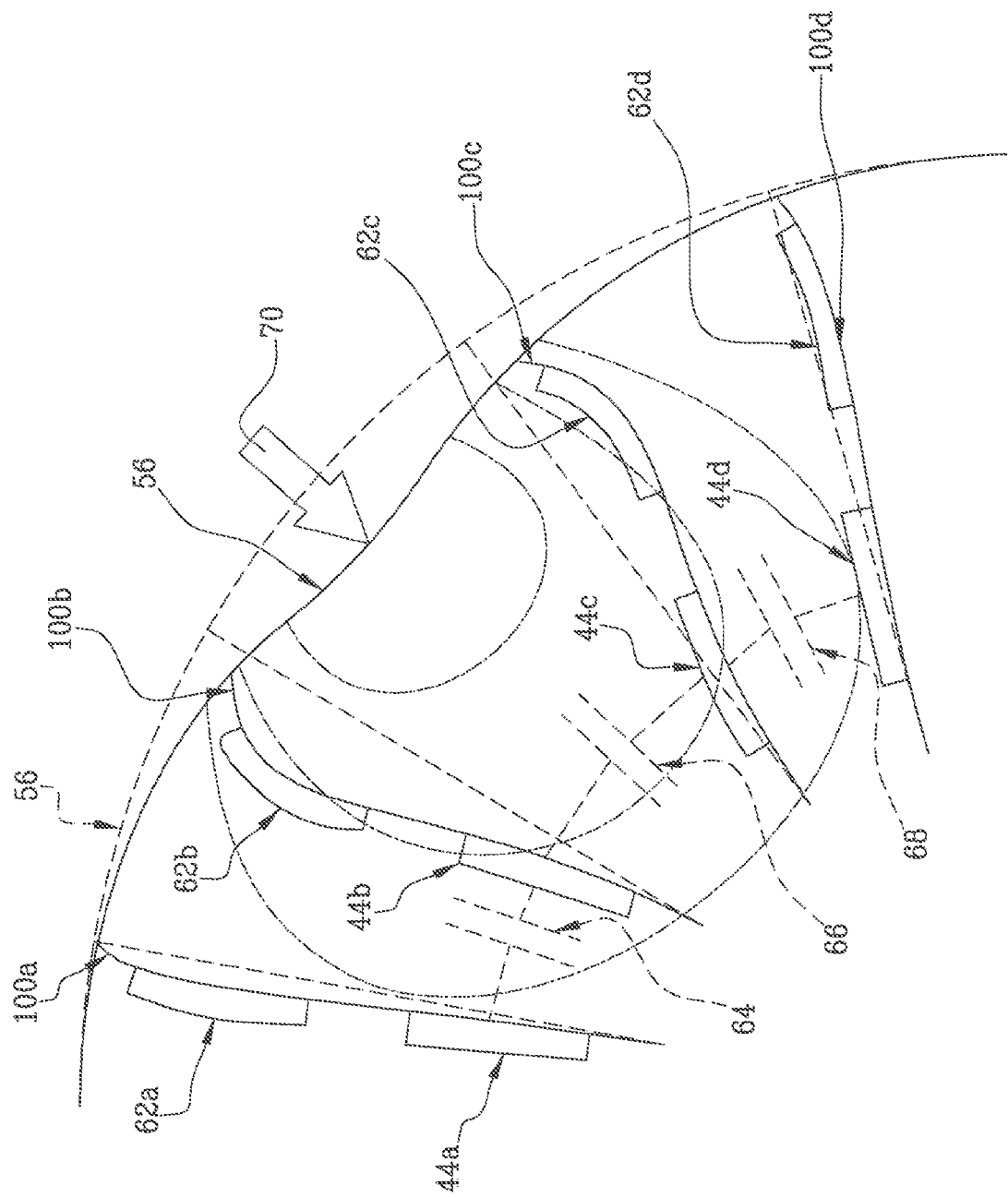
FIG. 9 shows the effect of a force on the cross section in FIG. 8.

FIG. 9 shows the effect, on the cross section in FIG. 8, of a force, indicated by the arrow 70, exerted on an area of the hemispherical cap 56 of the flex-PCB sensor 100 and directed towards the inside of the flex-PCB sensor 100. The rest position of the hemispherical cap 56 is shown in FIG. 9 as a broken line, as are the rest positions of the four layers 100*a*, 100*b*, 100*c* and 100*d*. The first metal plate 44*a* and the second metal plate 44*b* are both shifted outwardly in the same direction, but the second metal plate 44*b* is shifted to a larger degree than the first metal plate 44*a*, being closer to the force 70 and in an area with a higher concentration of pressure. Therefore, the distance between the metal plates 44*a* and 44*b* narrows and the capacitance of the first capacitor 64 increases. The third capacitor 68 increases its capacitance for the same reason, in contrast, the capacitance of the second capacitor 66 decreases, because the reciprocal distance between the second metal plate 448*b* and the third metal plate 44*c* increases, given that they are shifted in opposite directions by the force 70.

Figure 10:
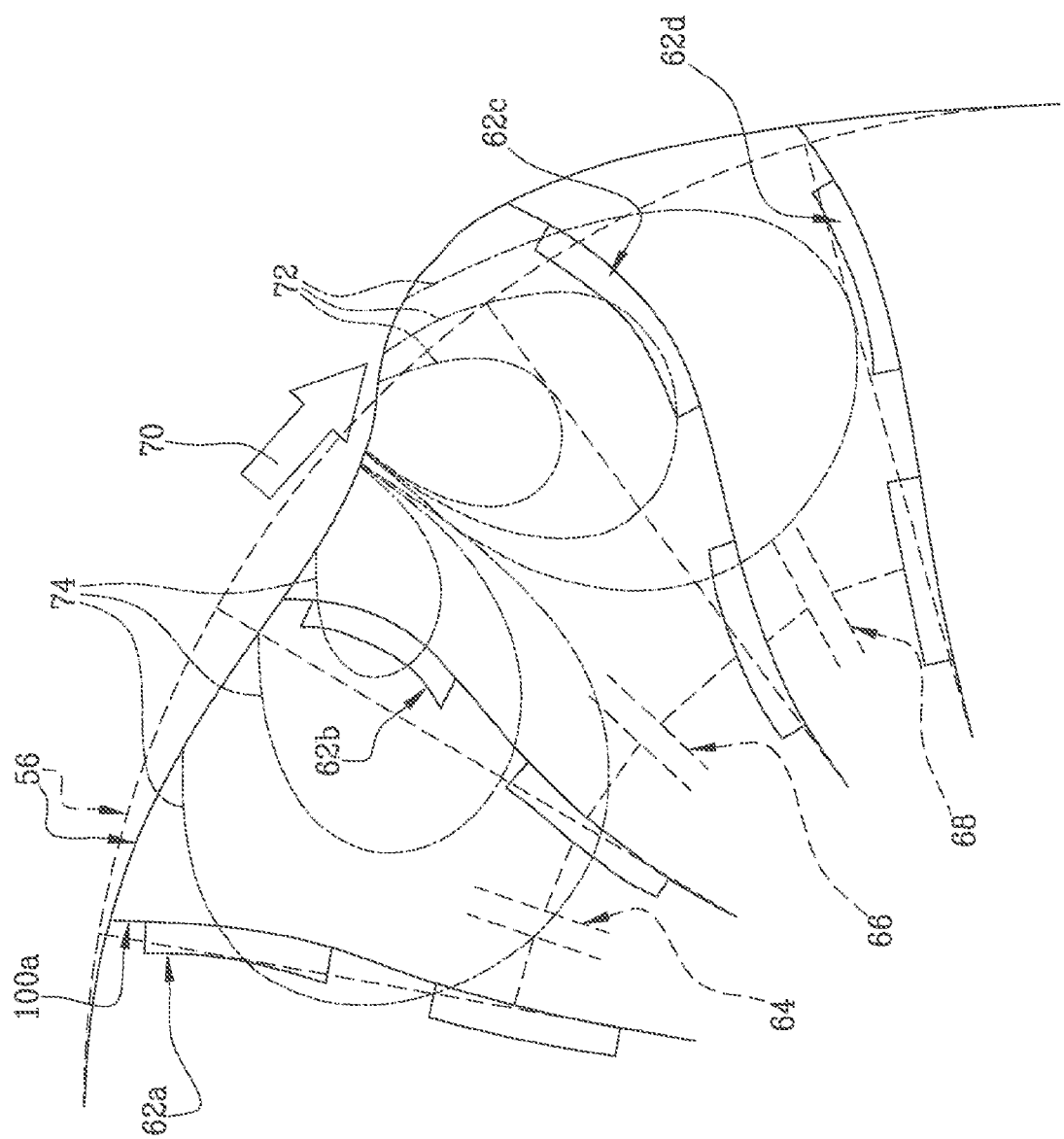
FIG. 10 is similar to FIG. 9 but it shows the effect of the force applied laterally along the surface of the flex-PCB sensor.

FIG. 10 is similar to FIG. 9 but shows the effect of the force 70 when applied laterally along the surface of the hemispherical cap 56 of the flex-PCB sensor 100. The shifting of the surface of the hemispherical cap 56 is shown as a continuous line, again with reference to a broken line which shows the rest state.

First broken lines 72 shows zones of a pressure increase corresponding to the zones where the force 70 is exerted, whereas second broken lines 74 show zones of a decrease in that pressure in the area below and behind the force 70. The third and fourth sensitive elements 62*c* and 62*d* undergo an increase in pressure, whereas the first and second sensitive elements 62*a* and 62*b* undergo a decrease in pressure. The capacitors 64 and 66 have a decrease in capacitance whereas the capacitor 68 has an increase in capacitance.

Considering the scenarios in FIGS. 9 and 10, whilst it can be difficult to deduce something from the measurement of a single sensitive element 62*a*, 62*b*, 62*c* and 62*d*, the measurements coming from different sensitive elements 62*a*, 62*b*, 62*c* and 62*d* during the application of the force 70 provide information that makes it possible to determine spatiotemporal models of such forces.

A second embodiment will now be shown, wherein two flex-PCB sensors 100 are associated so as to form a single sensor.

Figure 11:
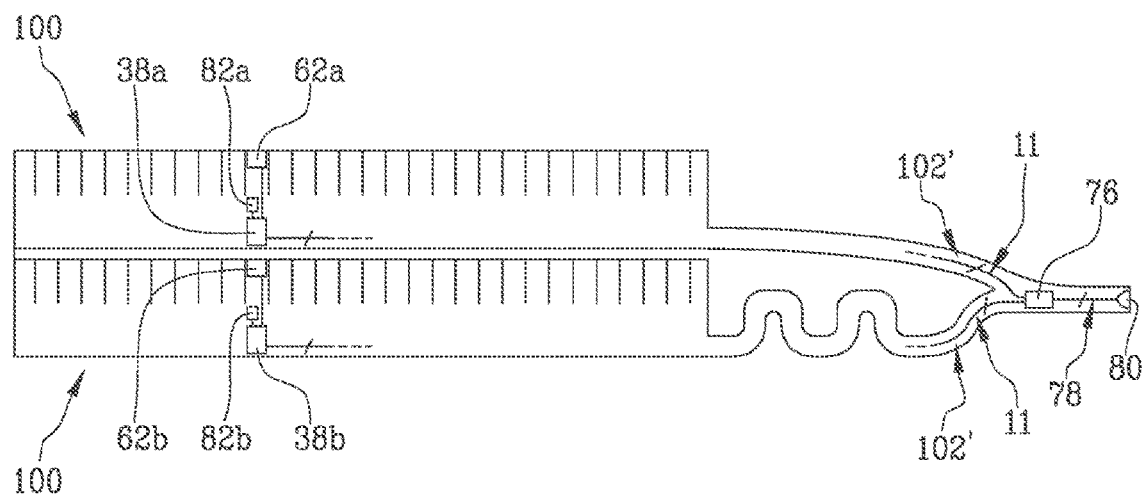
FIG. 11 shows a top view of two flex-PCB sensors placed side by side.

FIG. 11 shows a top view of two flex-PCB sensors 100 of the above-described type placed side by side, advantageously printed on a same substrate. The respective protuberances 102' carry respective connection buses 11 that are joined in a coupling circuit 76 whose function is to join the two connection buses 11 into a single common bus 78, which eventually terminates in a common connector 80. In general, a plurality of buses can be joined together to create a single common bus 78.

A single sensor cell 14, 16, . . . , 18 is shown in detail on every flex-PCB sensor 100. The sensitive element 62*a*, the circuit 38*a* and a first communication element 82*a*, described below, are shown on the flex-PCB sensor 100 at the top. The sensitive element 62*b*, the circuit 38*b* and a second communication element 82*b* are shown on the flex-PCB sensor 100 at the bottom, though said second communication element 82*b* can have a different form, as described below.

Figure 12:
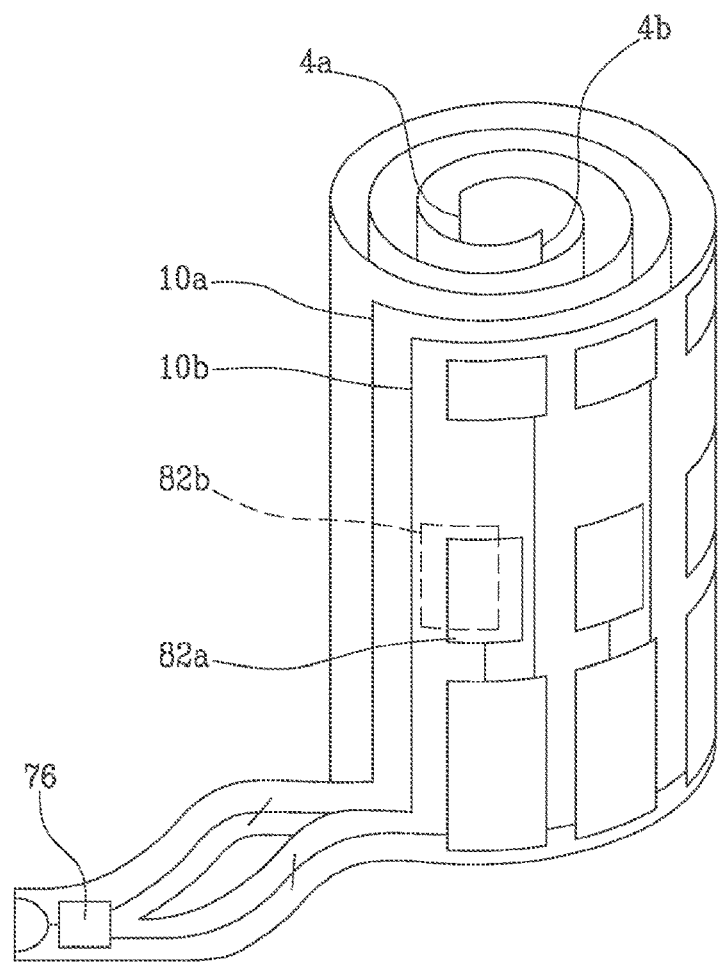
FIG. 12 shows the flex-PCB sensors in FIG. 11 wound into an intertwined coil structure.

FIG. 12 shows the flex-PCB sensors 100 in FIG. 11 wound into an intertwined coil structure. The references 4*a* and 4*b* indicate a first and a second inner side of each flex-PCB sensor 100. The first inner side 4*a* is connected to a first outer side 10*a*, whereas the second inner side 4*b* is connected to the second outer side 10*b*.

The first communication element 82*a*, shown with a solid border, is on the outermost surface close to the second outer side 10*b*, whereas the second communication element 82*b*, whose border is shown with a broken line, is positioned below said outer surface, close to the first outer side 10*a*. It can be seen that the first and second communication elements 82*a* and 82*b* lie parallel on layers that are tightly wound and at least partially overlap.

Advantageously, the first and second communication elements 82*a* and 82*b* are conductive plates separated by a layer of insulating material and the capacitor they form can be used to provide pulse communications. Alternatively, the first communication element 82*a* is a light-emitting diode and the second communication element 82*b* is a photosensitive component, so as to obtain a photonic communication.

In this embodiment it is possible that various separate circuits 38 placed on adjacent layers can interfere with one another in undesirable ways, therefore, an electric or optical shield is advantageously present between the regions of different flex-PCB sensors 100 where communication is not desired.

One of the main advantages of the present invention is that there exists a great variety of sensing techniques that can be implemented on the flex-PCB sensor 100 through printing processes.

An active infrared proximity sensing process will now be described, as an application of the present invention.

Figure 13:
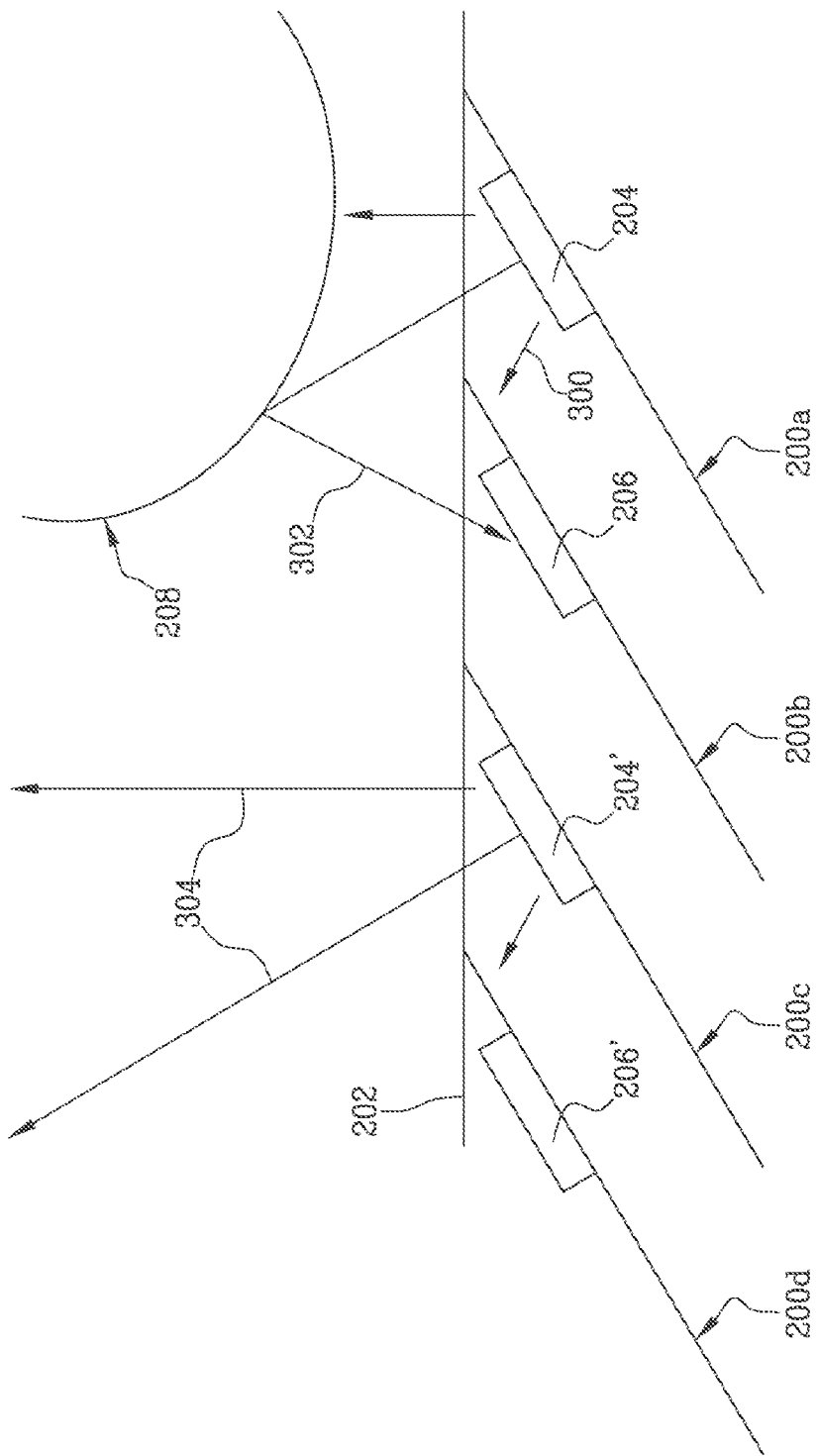
FIG. 13 shows a cross section of a set of flex-PCB sensors configured to create a sensing surface.

FIG. 13 shows a cross section of a set of flex-PCB sensors 200*a*, 200*b*, 200*c* and 200*d* as described above, designed to create a sensing surface 202, which they intersect with a predetermined acute angle. A light-emitting diode (LED) 204 is positioned on the first flex-PCB sensor 200*a*, whereas a photodiode 206 is positioned on the second flex-PCB sensor 200*b*. Where the second flex-PCB sensor 200*b* is opaque, there is no direct path for the light to travel between the diode 204 and the photodiode 206, as shown by a first ray of light 300. In contrast, a second ray of light 302 emitted by the diode 204 is reflected by an object 208 and received by the photodiode 206. The references 204' and 206' respectively indicate a second diode and a second photodiode. A third ray of light 304 emitted by the second diode 204' is not reflected by the object 208, nor received by the second photodiode 206'.

Various techniques are known in which the detection of light inside a tactile sensor can be used to deduce information about the deformations the sensor itself undergoes due to the pressure on its surface. The detection of light can be used, for example, to trace the movement of markers within a deformable flexible sensor.

In one variant of the invention, once a three-dimensional structure with the flex-PCB sensor 100 as described above has been created, a transparent epoxy resin is injected into the internal spaces of the flex-PCB sensor 100 to lend a solid, rigid form to the flex-PCB sensor 100.

Figure 14:
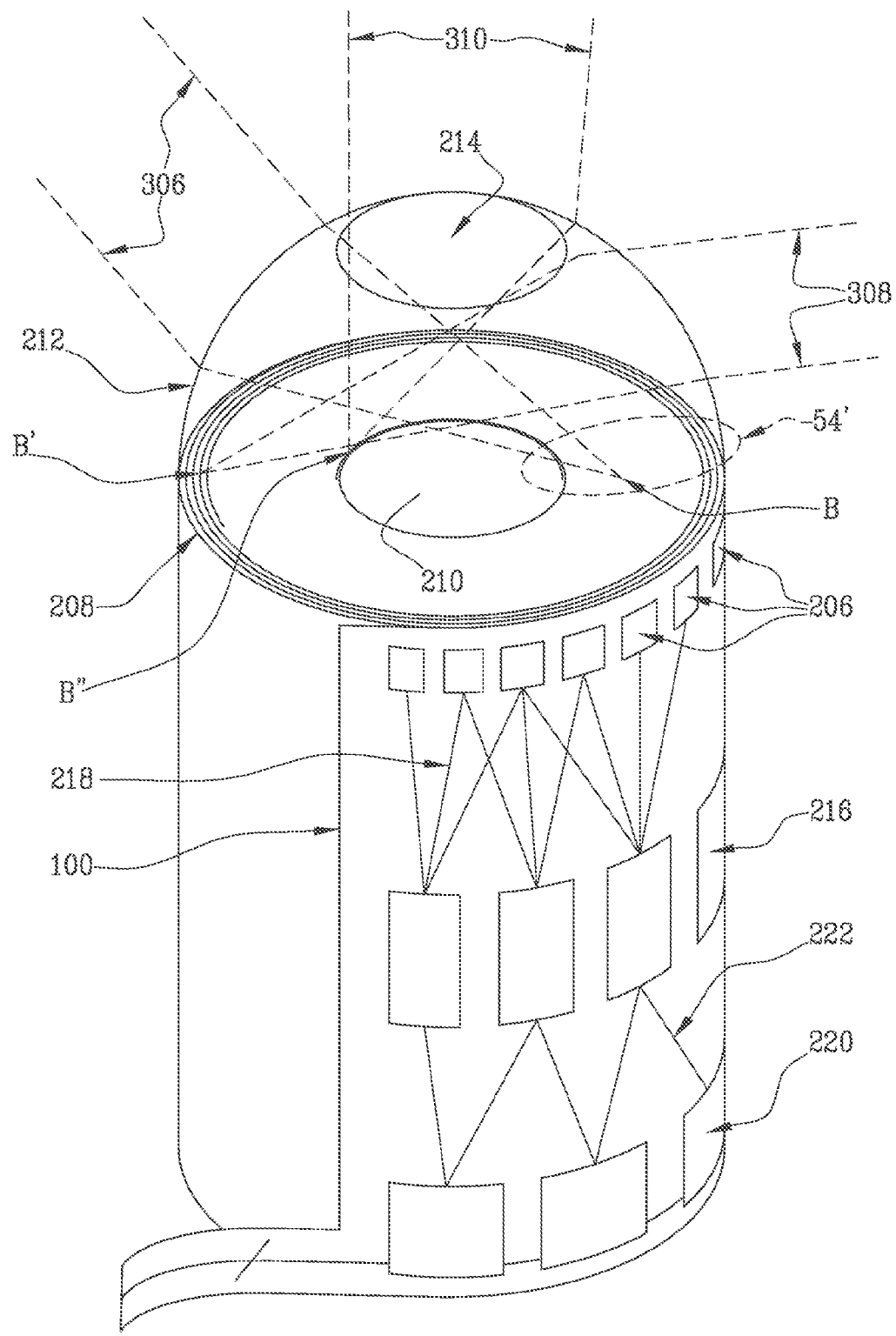
FIG. 14 shows a three-dimensional sensor based on the flex-PCB sensor.

FIG. 14 shows a three-dimensional sensor formed with a coiled flex-PCB sensor 100 as described above.

The flex-PCB sensor 100 comprises a series of sensitive elements 206 aligned along the sensitive side 20. The sensitive elements 206 contain at least one photodiode, and optionally other circuits for signal transduction; hereinafter they are indicated only as photodiodes for the sake of simplicity. The flex-PCB sensor 100 is tightly wound into a coil shape, so that the photodiodes 206 are close to an upper circular sensing border 54' of the coil, preferably around a cylindrical template 210. In particular, the upper circular sensing border 54' is a surface formed by placing side by side many layers of the sensitive side 20 coiled around the template 210. The cuts 22a, 22b, . . . , 22n are not present between the photodiodes 206.

A printed element 212, preferably made of a transparent material such as epoxy resin, is fixed on top of the upper circular border 208. The printed element 212 is a focusing element: parallel rays of light 306 incident upon the flex-PCB sensor 100 are focused on a first zone B of the upper circular sensing border 54'; similarly, rays 308 coming from the opposite side are focused on a second zone B'. The photodiodes 206 thus represent the pixels of a vision sensor, wherein every photodiode 206 measures the light incident upon the flex-PCB sensor 100, or the variations thereof. A lens 214 is positioned on top of the printed element 212; parallel rays of light 310 oriented along the axis of the template 210 are focused by the lens 214 onto a third zone B" located at the circumference of the template 210. Processing circuits 216, positioned below the photodiodes 206, receive signals from the photodiodes 206 by means of a plurality of first connection wires 218. The first connection wires 218 in FIG. 14 suggest cross relations among the various components; however, there could instead be simple unidirectional wiring or a communication infrastructure of arbitrary complexity. The processing circuits 216 are adapted to perform visual processing of the signals received. Finally, a plurality of final circuits 220, connected to the processing circuits 216 by means of respective second connection wires 222, prepare respective output signals.

Figure 15:
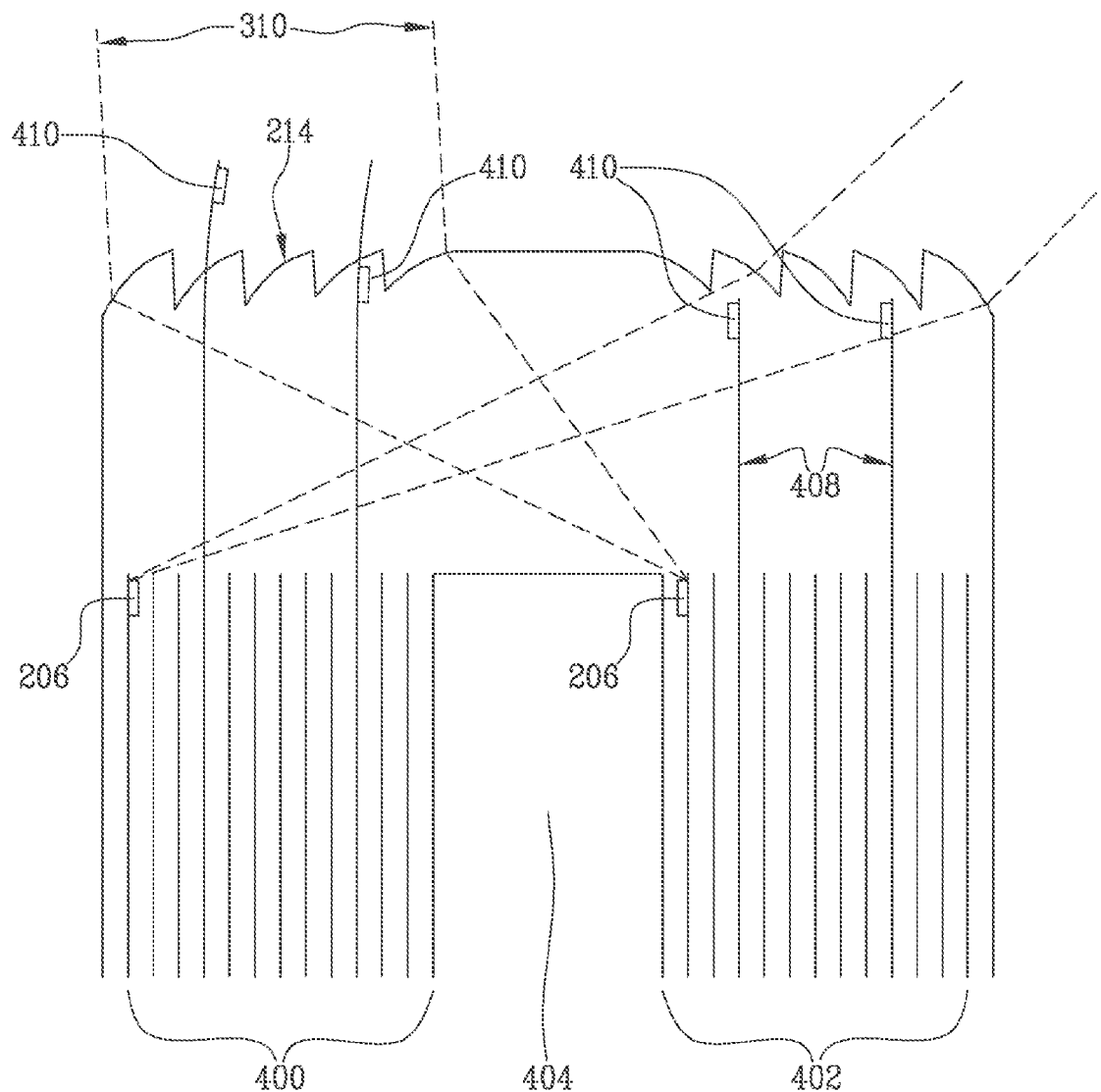
FIG. 15 shows a cross section of a device similar to the one in FIG. 14.

FIG. 15 shows a cross section of a device similar to the one in FIG. 14.

The references 400 and 402 indicate coiled layers of flex-PCB sensors 100, whereas 404 indicates the space occupied by the central template. In this embodiment the lens 214 is a Fresnel lens and the parallel rays of light 310 are focused on the photodiode 206.

Rectangular extensions 408 of the flex-PCB sensors 400, 402 are likewise present; they extend upwards beyond the sensitive side 20, allowing pressure sensors 410 to be positioned close to the lens 214. Alternatively, the extensions 408 project through the lens 214, forming bristle-like elements. In this manner, the extensions 408 can reach or go beyond the lens 214, thereby making the surface of the sensor sensitive to touch. In this manner, one obtains a sensor that is simultaneously visual and tactile.

Various embodiments of the present invention have been presented wherein the flex-PCB sensor 100 is coiled in the third dimension to create a three-dimensional structure; however, any type of configuration resulting in a three-dimensional multilayer structure, wherein some borders of said layers define a sensing one, is included within the scope of the present invention.

FIG. 16 shows a flex-PCB sensor 100 similar to the one in FIG. 1, with sensitive elements 500 arranged along the sensitive side 20. In this example, the cuts 22a, 22b, . . . , 22n are present, but so are additional cuts 23a, 23b, . . . 23n, which project upwards on the circuit side 2.

FIG. 17 shows a three-dimensional structure that uses the flex-PCB sensor in FIG. 16.

Starting from an outer border 600 a first continuous strip is made in an accordion-like form and extends prevalently in a first dimension 602. Then the strip is doubled over itself, extending in a second dimension 604 perpendicular to the first dimension 602. The cuts 22a, 22b, . . . , 22n of the first strips each fit together with a respective additional cut 23a, 23b, . . . , 23c of the second strip.

Such a configuration can be useful for creating broad coverages of sensitive areas, for example protective covers for robots. Alternatively, such a configuration can be useful for creating arrays of sensors that permit the passage of a flow of gas through them.

An alternative embodiment of the flexible printed circuit sensor according to the present invention will now be presented.

Figure 18:
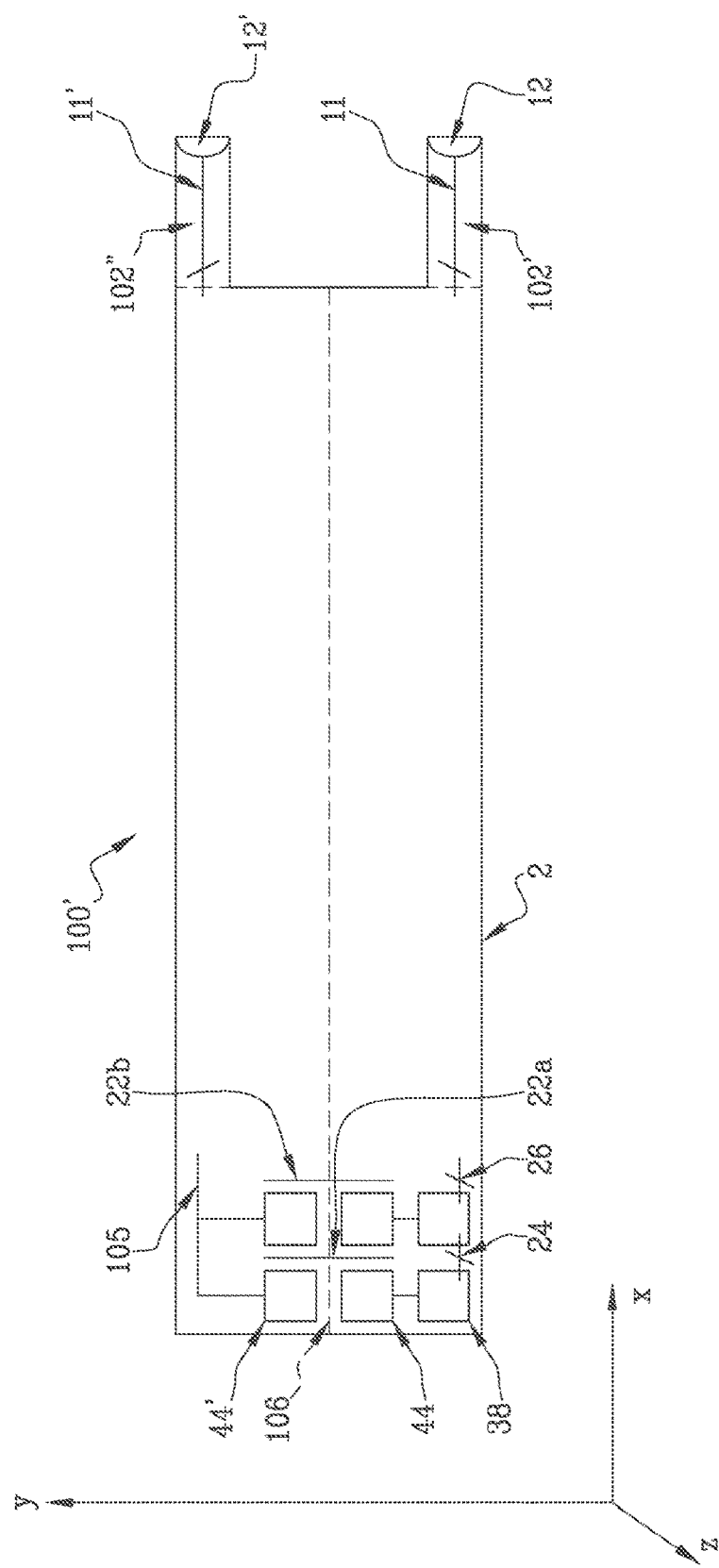
FIG. 18 shows a top view of a flex-PCB sensor similar to the one illustrated in FIG. 1.

FIG. 18 shows a top view of a flexible printed circuit flex-PCB sensor 100' similar to the one illustrated in FIG. 1, wherein similar elements have the same reference.

A second additional metal plate 44' is printed on top of the first additional metal plate 44 already described with reference to FIG. 1, along the second axis (y axis); it is connected by means of a single common connection wire 105 to respective second additional metal plates 44' present in adjacent sensor cells 14, 16, . . . , 18, eventually reaching an additional protuberance 102" which accommodates a respective additional connection bus 11' directed towards the remote processing circuit by means of an additional connector 12'.

The additional plates 44 and 44' are internally conductive but are covered by a thin insulating layer. After the printing process, the flex-PCB sensor 100' is suitable for being bent along a central axis 106 (in the direction of the x axis). This bending, carried out after the printing step but before lamination, has the effect of bringing the first additional plates 44 and the second additional plates 44' into close proximity along a third dimension (z axis).

Figure 19:
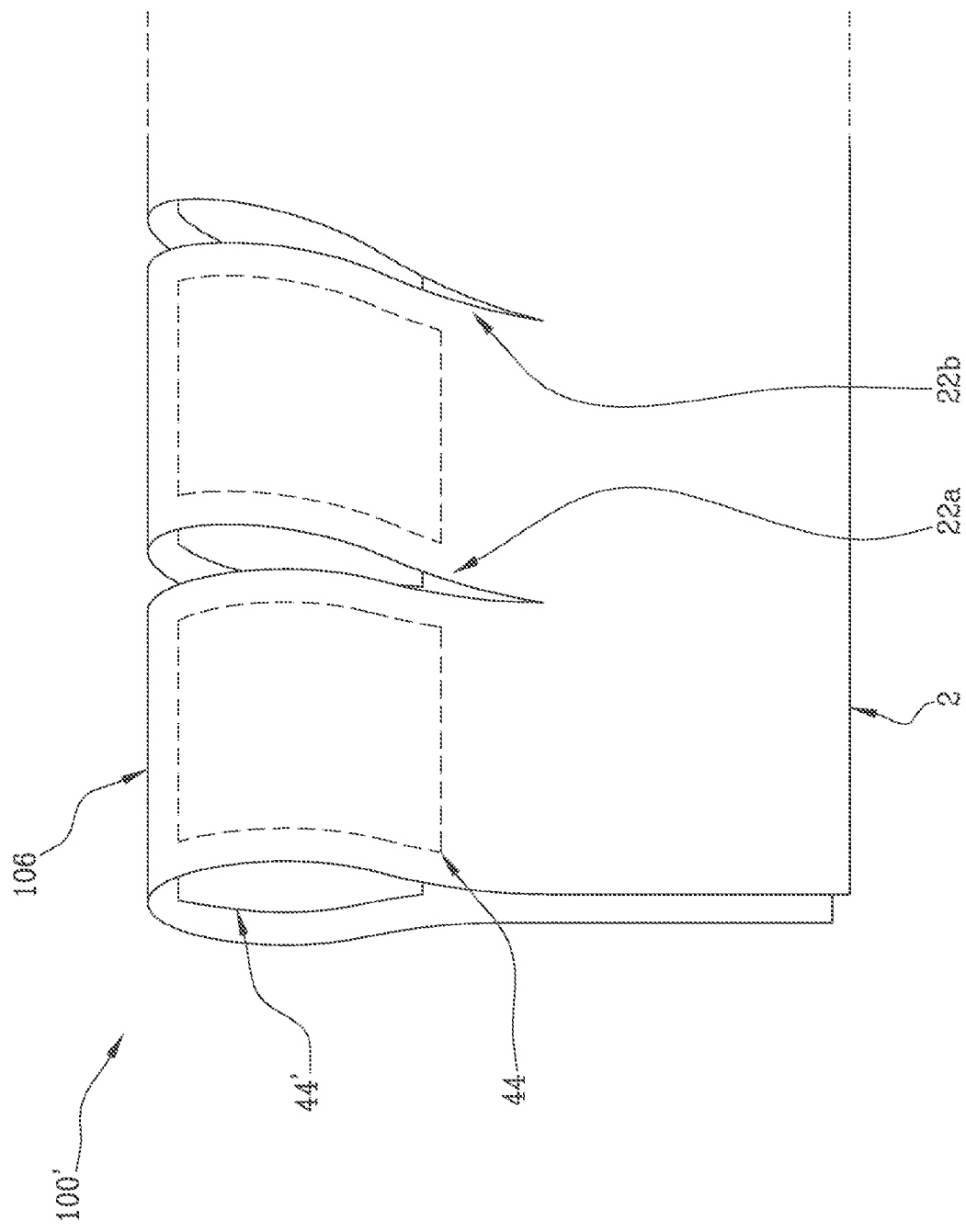
FIG. 19 shows the flex-PCB sensor after bending.

FIG. 19 shows the flex-PCB sensor 100' after bending along the central axis 106. The first additional plate 44 (facing towards the inside and shown with a broken line) is facing towards the second additional plate 44' and forms a capacitor. If the second additional plates 44' are all maintained at a preselected tension by means of the common connection wire 105 in FIG. 18, a variation in the distance between the first and second additional plates 44 and 44' will result in a variation in the capacitance detectable by an appropriately selected transduction circuit (circuit 38). The cuts 22a, 22b, . . . , 22n now offer each capacitor an independent mobility in the third dimension.

Figure 20:
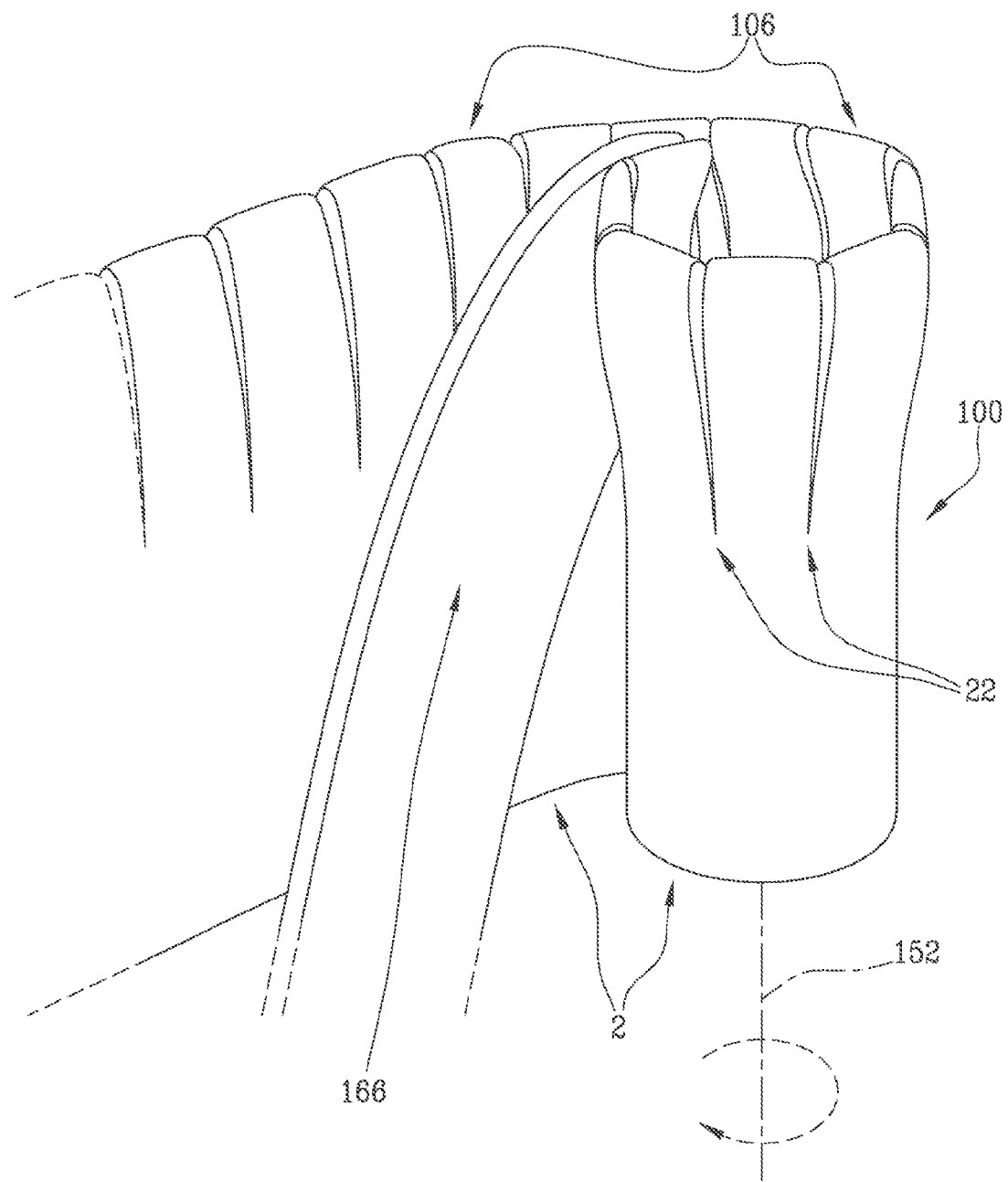
FIG. 20 shows the main step of three-dimensional configuration.

FIG. 20 shows the main three-dimensional configuration step: a winding about a central axis 152, preferably using a cylindrical jig (not shown in the figure). Optionally, a strip of spongy material 166 is inserted between the individual layers of sensitive elements.

FIG. 21 shows a cross sectional view of the flex-PCB sensor 100' in FIG. 20.

The lower part of the flex-PCB sensor 100' contains all the circuitry part, i.e. the circuit side 2 and the part of the flex-PCB sensor 100' that contains the common connection wire 105, which has been bent downwards in the direction of the y axis in FIG. 18. The central axis around which the flex-PCB sensor 100' has been wound is indicated with the reference 400. The capacitors are shown in cross section, each is formed by two facing additional plates 44 and 44'. The distance between these additional plates 44, 44' is the result of a combination of the internal mechanical tension in the bent flex-PCB sensor 100', the compression of the spongy insert 166 and any other external force. The insulating layer present on the additional plates 44, 44' prevents them from creating a conductive connection even if they touch. The central axis 106 now faces outwardly. A broken line 168 that joins the tips of the sensor cells along the central axis 16 represents the sensing surface. Mechanical forces transmitted through the sensing surface are capable of modifying the distances between the additional plates 44, 44', causing a variation in capacitance across the surface of the flex-PCB sensor 100', which can be detected and transmitted by the sensor cells and the associated circuits 38.

The main advantage of the flex-PCB sensor 100 of the present invention is the fact that it is produced with a two-dimensional printing process, is flexible and contains sensitive elements and transduction, processing, and communication circuits. The flex-PCB sensor 100 is suitable for being used to produce three-dimensional surfaces for different types of sensing, despite containing large quantities of circuits in a compact form. In particular, the sensitive elements can be easily placed at different depths relative to the sensing surface.

The flex-PCB sensor 100 of the present invention is produced using a simple, economical technology with a high iteration speed thanks to the two-dimensional printing process, as compared to alternatives of integrated circuits manufactured with molten silicon, the production of three-dimensional stacked silicon chips or the use of three-dimensional printing techniques. When the circuits associated with the sensitive elements are placed at greater depths than the sensitive elements themselves, they can benefit from protection against environmental influences.

In general, signal transduction and processing can be performed in parallel in a distributed manner throughout the flex-PCB sensor 100 and communication can take place between different layers of the sensor itself, in order to construct a three-dimensional computational architecture.

These sensors can also be completely biodegradable.

Naturally, without prejudice to the principle of the invention, the forms of implementation and details of construction can vary widely with respect to what has been described and illustrated purely by way of non-limiting example, without going beyond the scope of protection of the present invention defined by the appended claims.

The design from which the present patent application derives received funding under the European Union's research and innovation programme Horizon 2020, contract no. 813713.

The invention claimed is:

1. A flexible printed circuit flex-PCB sensor comprising:
   at least one sheet of electronically printable flexible material;
   sensor cells printed on said at least one sheet and each sensor cell comprising at least one sensitive element and a circuit, wherein each sensitive element is arranged to measure a predetermined physical parameter and to obtain an associated measurement signal, and each circuit is arranged to receive said measurement signal and to process said measurement signal in order to obtain a corresponding output signal;
   communication means connected to said sensor cells and arranged to transmit the digital signals coming from said sensor cells to a remote processing circuit;
   wherein said at least one sheet is coiled according to a three-dimensional shape comprising a layered structure, wherein a plurality of layers of said sheet are placed side by side and form, in a region defined by sensing borders of the coiled and placed side by side plurality of layers, a sensing surface, said sensitive elements of each sensor cell being placed close to said sensing surface and said sensing surface being substantially perpendicular to the surface of said sheet.

2. The sensor according to claim 1, wherein each sensitive element is positioned closer to the sensing border than the circuit.

3. The sensor according to claim 1, wherein the sensitive elements are placed at different depths relative to the sensing border.

4. The sensor according to claim 1, wherein said physical parameter comprises pressure, electric, magnetic or photonic conditions or chemical concentrations.

5. The sensor according to claim 1, wherein each sensor cell comprises a first plate and a second plate of conductive material made so as to be superimposed one upon the other and between the first plate and the second plate there is a layer of piezoelectric material, said first plate and second plate forming overall the sensitive element.

6. The sensor according to claim 1, wherein the digital signals processed by the circuit are suitable for being sent, by means of adjacent sensor cells, to the remote processing circuit through a connector.

7. The sensor according to claim 1, wherein each sensor cell further comprises an additional metal plate which represents an additional sensitive element, placed farther from the sensing border than the respective sensitive element but closer to it than the circuit.

8. The sensor according to claim 1, comprising two sheets of electronically printable flexible material placed side by side, each comprising a plurality of sensor cells each comprising at least one sensitive element, a circuit and a communication element, wherein said sheets of electronically printable flexible material are adapted to be wound into an intertwined coil structure so that a first communication element and a second communication element lie parallel on layers that are tightly wound and at least partially overlapping.

9. The sensor according to claim 8, wherein the first communication element and the second communication element are conductive plates separated by a layer of insulating material, or the first communication element is a light-emitting diode and the second communication element is a light-sensitive component, so as to obtain a photonic communication.

10. The sensor according to claim 1, wherein the sheet of electronically printable flexible material is adapted to be inserted into a hemispherical mould suitable for receiving an elastomeric material, so that the flex-PCB sensor is inserted inside a solid elastomeric hemisphere.

* * * * *